US006213973B1

(12) United States Patent
Eliasen et al.

(10) Patent No.: US 6,213,973 B1
(45) Date of Patent: Apr. 10, 2001

(54) VASCULAR ACCESS PORT WITH ELONGATED SEPTUM

(75) Inventors: Kenneth A. Eliasen, West Jordan; Kelly B. Powers, North Salt Lake, both of UT (US); Kelly J. Christian, Pocatello, ID (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/005,608

(22) Filed: Jan. 12, 1998

(51) Int. Cl.$^7$ ................................................... A61M 11/00
(52) U.S. Cl. ........................ 604/93.01; 604/175; 604/905; 604/890.01
(58) Field of Search ..................................... 604/93, 890.1, 604/891.1, 175, 93.01, 174, 905, 183, 244, 523; 178/DIG. 12

(56) References Cited

U.S. PATENT DOCUMENTS

| 3,853,127 | 12/1974 | Spademan . |
| 4,043,333 | 8/1977 | Munsch . |

(List continued on next page.)

FOREIGN PATENT DOCUMENTS

| 4423706 | 2/1996 | (DE) | ............................. A61M/5/152 |
| 332943 | 9/1988 | (EP) | ............................. A61M/37/00 |

OTHER PUBLICATIONS

Polyurethanes—The bridge between Silicone Rubbers and Plastics.*
C.R. Bard, Inc., Instructions for Use for BardPort® and SlimPort™ Implanted Ports with Open–Ended Catheters (Jun. 1997).
C.R. Bard, Inc., Ports: Setting the Standard with the Comprehensive Family of Ports (1999).
C.R. Bard, Inc., SlimPort™ Implanted Ports: The Complete Line of Low–Profile Ports (1999).
CPC, single reservoir plastic vascular access port Serial No. 205,129 (circa pre–1994).
C.R. Bard, Inc., disassembled prototype single reservoir metal vascular access port (circa 1994).
C.R. Bard, Inc., M.R.I.™ hard–base single reservoir vascular access port (circa pre–1993).

(List continued on next page.)

*Primary Examiner*—John G. Weiss
*Assistant Examiner*—LoAn H. Thanh
(74) *Attorney, Agent, or Firm*—Trask Britt

(57) ABSTRACT

An elongated access port has a needle-impenetrable housing enclosing a fluid reservoir. The housing includes a base having a floor with an upstanding encircling sidewall and a cap having a top wall with a depending encircling skirt. The skirt of the cap receives the sidewall of the base. An access aperture extends through the top wall of the cap to communicate with the fluid reservoir. The access aperture is encircled by a continuous rim having an elongated shape in the plane of the access aperture. The rim of the access aperture may be elliptical, oval, polygonal, or parabolic-ended. An elastomeric, needle-penetrable, generally planar septum is disposed in the access aperture with the periphery of the septum in sealing engagement with the rim of the access aperture. Prior to installation, the septum has a periphery with a cross section in the plane of the septum that is geometrically proportional to and larger than the shape of the access aperture. Installation causes the periphery of the septum to be displaced inwardly by the rim of the access aperture in a direction parallel to the plane of the septum. In view of the relative shapes of the rim of the access aperture and the periphery of the septum, this produces substantially uniform hydrostatic pressure in regions of the installed septum that are subjected in use of the access port to needle penetrations. Opposite faces of the periphery of the septum are urged toward each other between the cap of the housing and the top of the sidewall of the base of the housing.

88 Claims, 12 Drawing Sheets

U.S. PATENT DOCUMENTS

| | | |
|---|---|---|
| 4,496,350 | 1/1985 | Cosentino . |
| 4,692,146 | 9/1987 | Hilger . |
| 4,710,167 | 12/1987 | Lazorthes . |
| 4,772,270 * | 9/1988 | Wiita et al. ............................ 604/175 |
| 4,781,695 | 11/1988 | Dalton . |
| 4,802,885 * | 2/1989 | Weeks et al. ............................ 604/93 |
| 4,834,720 * | 5/1989 | Blinkhorn ............................ 604/244 |
| 4,904,241 * | 2/1990 | Bark ........................................ 604/93 |
| 4,915,690 | 4/1990 | Cone et al. . |
| 4,978,338 * | 12/1990 | Melsky et al. ........................... 604/93 |
| 5,013,298 * | 5/1991 | Moden et al. ........................... 604/93 |
| 5,026,344 * | 6/1991 | Dijkstra et al. ......................... 604/93 |
| 5,041,098 * | 8/1991 | Loiterman et al. ................... 604/175 |
| 5,045,060 * | 9/1991 | Melsky et al. ........................... 604/93 |
| 5,085,644 * | 2/1992 | Wattson et al. ....................... 604/153 |
| 5,090,954 * | 2/1992 | Geary ...................................... 604/29 |
| 5,108,377 | 4/1992 | Cone et al. . |
| 5,167,638 | 12/1992 | Felix et al. . |
| 5,185,003 * | 2/1993 | Brethauer ............................... 604/93 |
| 5,213,574 * | 5/1993 | Tucker .................................... 604/93 |
| 5,318,545 * | 6/1994 | Tucker .................................. 604/244 |
| 5,360,407 * | 11/1994 | Leonard ................................ 604/175 |
| 5,399,168 | 3/1995 | Wadsworth, Jr. et al. . |
| 5,476,460 * | 12/1995 | Montalvo ........................... 604/891.1 |
| 5,562,617 * | 10/1996 | Finch, Jr. et al. ..................... 604/93 |
| 5,575,770 * | 11/1996 | Melsky et al. ........................... 604/93 |
| 5,607,393 * | 3/1997 | Ensminger et al. .................... 604/93 |
| 5,695,490 * | 12/1997 | Flaherty et al. ................... 604/891.1 |
| 5,718,682 * | 2/1998 | Tucker .................................... 604/93 |
| 5,833,654 | 11/1998 | Powers et al. .......................... 604/93 |
| 5,848,989 * | 12/1998 | Villani .................................... 604/93 |
| 6,086,555 | 7/2000 | Eliasen et al. ........................... 604/93 |

OTHER PUBLICATIONS

C.R. Bard, Inc., M.R.I.® low–profile single reservoir vascular access port Serial No. 7835 (circa pre–1994).

C.R. Bard, Inc., M.R.I™ single reservoir vascular access port Serial No. 2068 (circa pre–1993).

C.R. Bard, Inc., RADSTIC™ radiology microintroducer kit (circa Mar. 1998).

C.R. Bard, Inc., Rosenblatt™ dual reservoir SlimPort™ vascular access port Serial No. TM00108 (circa May 1997).

C.R. Bard, Inc., SlimPort™ M.R.I.® ultralow–profile vascular access port kit (circa Feb. 1999).

C.R. Bard, Inc., SlimPort™ single reservoir vascular access port Serial No. TB02168 (circa Aug. 1998).

C.R. Bard, Inc., titanium single reservoir vascular access port Serial No. 4404292(circa pre–1992).

C.R. Bard, Inc., Ultra SlimPort™ single reservoir vascular access port Serial No. 0987 (circa Feb. 1999).

Davol, Inc., titanium low–profile single reservoir vascular access port Serial No. TS48940 (circa pre–1990).

Davol, Inc., titanium single reservoir vascular access port Serial No. 8108637 (circ pre–1992).

Harbor Medical, Inc., TopSider™ single reservoir vascular access port Serial No. 522,901 (circa pre–1994).

Infusaid, Inc., single reservoir vascular access port Serial No. 224107 (circa pre–1990).

Norfolk Medical, Inc., single reservoir vascular access port Serial No. 01L01 (circa pre–1994).

Pharmacia Deltec, Port–a–Cath™ Pasport single reservoir vascular access port (circa pre–1990).

Strato Corp., single reservoir vascular access port sectioned to reveal internal structure (circa pre–1995).

Therex Corporation, R–Port® single reservoir vascular access port Serial No. 9563 (circa 1994).

Instructions for Use, Therex® R–Port® Implantable Vascular Access System, Therex Corporation, Walpole, MA 02081.

* cited by examiner

VASCULAR ACCESS PORT WITH ELONGATED SEPTUM

BACKGROUND OF THE INVENTION

1. The Field of the Invention

The present invention relates to vascular access systems and, more specifically, to implantable vascular access ports for use in such systems.

2. Background Art

Implantable vascular access systems are used extensively in the medical field to facilitate the performance of recurrent therapeutic tasks inside the body of a patient.

Such a vascular access system generally includes an implantable vascular access port attached to the proximal end of a vascular catheter. A typical vascular access port has a needle-impenetrable housing that encloses a fluid reservoir that is accessible from the exterior of the access port through a needle-penetrable elastomeric septum. The vascular access port also includes an outlet stem, which projects from the housing and encloses a fluid passageway that communicates with the fluid reservoir. The distal end of the catheter is mechanically coupled to the vascular access port in fluid-tight communication with the fluid reservoir using the outlet stem.

The entirety of the system, both the vascular access port and the catheter attached thereto, is implanted in the body of a patient. The distal tip of the catheter is disposed at a predetermined location where therapeutic activity is to be effected. The distal tip of the catheter is either open-ended or is provided with pressure-sensitive valving that affords for one-way or two-way fluid flow therethrough during use of the system by medical personnel. Once the vascular access system is implanted, the tip of a hypodermic needle can then be employed selectively and repeatedly to access the fluid reservoir of the access port by penetrating the skin at the implantation site for the access port and then by being advanced through the septum of the access port itself.

The syringe associated with the hypodermic needle then is able to deliver medication or other fluids into the fluid reservoir. These flow through the outlet stem of the vascular access port and through the catheter attached thereto, thereby to become infused into the body of the patient at the distal tip of the catheter. Alternatively, the syringe is able to aspirate bodily fluids from the vicinity of the distal tip of the catheter by withdrawing such fluids along the catheter, through the outlet stem and the fluid reservoir of the vascular access port, and lastly up the hypodermic needle into the syringe.

For the repeated selective use of an implanted vascular access port to be successful in the long term, the septum of that vascular access port be possessed of specific properties.

For example, when the tip of a hypodermic needle penetrates the septum, the material of the septum about the shaft of the hypodermic needle must form an effective seal about the exterior of that needle. Otherwise, fluid will escape from the fluid reservoir to the exterior of the vascular access port along the exterior of the shaft of the hypodermic needle. This needle sealing characteristic of the septum of a vascular access port is influenced by several factors, a few of which will be explored subsequently.

The septum should also impose a predetermined amount of needle retention force on the shaft of any hypodermic needle that has penetrated therethrough. Needle retention force refers to the tendency of a septum to resist the removal therefrom of the shaft of any such hypodermic needle. Inadequate needle retention force can allow the tip of the shaft of a hypodermic needle to become withdrawn inadvertently from a septum, even after the tip of the shaft of the hypodermic needle has penetrated the septum to the fluid reservoir in the vascular access port. This is quite painful to the patient and disruptive of the therapeutic process.

If the withdrawal of the hypodermic needle is detected, the attention of medical personnel will, at the very least, need to be redirected to the penetration of the tip of the hypodermic needle through the septum of the vascular access port. If the inadvertent withdrawal of the tip of the shaft of the hypodermic needle from the septum is not detected, however, fluids in the syringe associated with the hypodermic needle will not even enter the fluid reservoir of the vascular access port when infusion of those fluids is undertaken. Instead, the fluids will be injected subcutaneously into the pocket in which the vascular access port is implanted. Necrosis of the tissue surrounding the implantation pocket will occur as a result, complicating therapeutic activities and frequently requiring the removal and reimplantation at another site of the entire vascular access system.

A corollary aspect of the needle retention force imposed on the shaft of a hypodermic needle by any given septum is the degree of force required to cause the tip of that hypodermic needle to advance through the septum from the exterior surface to the interior surface thereof.

This is referred to as the needle penetration force. The needle retention force and the needle penetration force for a given septum are generally identical, but oppositely directed.

It is desirable that the amount of the needle penetration force.be within a range that facilitates the labors of medical personnel. First, the needle penetration force for a given septum cannot be substantial, or the process of accessing the fluid reservoir of the associated vascular access port with the tip of the shaft of a hypodermic needle will be difficult for medical personnel and dangerous to the patient.

On the other hand, the needle penetration force for a given septum should be distinctly different and usually greater than the force required to advance the tip of the shaft of a hypodermic needle through the tissue of the patient at the implantation site for the vascular access port. If such is the case, medical personnel utilizing a hypodermic needle to access the fluid reservoir in a vascular access port will be informed by feel when the tip of the hypodermic needle has actually encountered and is being advanced through that septum. Such tactile feedback has been reported to be particularly useful.

The sealing effectiveness, the needle retention force, and the needle penetration force for a given septum are each in part related to the amount and types of forces applied to the septum by the housing of the vascular access port in which the septum is installed. While torsional forces and tensions are on occasion applied to a septum by the housing of the vascular access port in which the septum is installed, it is more common that the forces applied thereto by a housing are directed inwardly toward the body of the septum. In general, the greater the inwardly directed forces that are applied to a septum, the greater will be the sealing effectiveness of the septum about the shaft of a hypodermic needle. Also, the larger will be the needle retention force and the needle penetration force that are imposed on the shaft of that hypodermic needle by that septum.

The inwardly directed forces imposed on an installed septum by the housing of a vascular access port must, however, not be so great that penetrating the septum with the tip of a hypodermic needle results in coring of the septum. When the tip of a hypodermic needle advances through the septum, coring occurs if any portion of the septum material is forced inside the shaft of the hypodermic needle through the opening in the tip thereof That portion of the septum material forced inside a hypodermic needle in this process is in effect severed from the rest of the body of the septum material.

S Septum coring produces small, detached particles of the septum that are likely to enter the fluid that is infused by the implanted vascular access system into the vascular system of the patient. These particles can obstruct fluid flow through the outlet stem of the vascular access port, or if escaping through the outlet stem of the vascular access port, can become trapped in the cardiovascular system of the patient.

In addition, septum coring produces small passageways through the body of a septum. On occasion these passageways extend entirely through the septum, from the exterior thereof to the fluid reservoir inside the vascular access port. The inwardly directed forces imposed on the installed septum by the housing of a vascular access port should initially urge the material of the body of the septum inwardly upon itself to close such passageways after the shaft of the hypodermic needle is withdrawn therefrom. Nonetheless, continued coring eventually leads to various forms of septum failure that cannot be overcome by such inwardly directed forces. The material continuity of the septum is increasingly compromised, resulting in crumbled areas of the septum matrix. Eventually, leakage of fluid can be expected through the septum from the fluid reservoir in the vascular access port. Once such fluid escapes to the exterior of the vascular access port, necrosis will occur of the tissue surrounding the subcutaneous pocket in which the vascular access port is implanted, causing consequences already described above.

The subcutaneous placement of a vascular access port makes it difficult to predict with precision the location in cross section of the septum of that vascular access port that will be penetrated by a hypodermic needle on any given occasion. The septum installed in the vascular access port should thus exhibit substantially uniform needle sealing, needle retention, and needle penetration characteristics across the entire area of the septum exposed to needle penetration. In this manner, the quality of the interaction between a septum and the shaft of a penetrating hypodermic needle will be substantially independent of the location at which the tip of the hypodermic needle actually enters the septum.

The desirability of producing uniform needle sealing, needle retention, and needle penetration characteristics in a septum has historically mandated that septums be circular in cross section. Uniform stress can be produced in the material of a circular septum by installing the septum in a circular access aperture that has an inner diameter that is smaller than the outer periphery of the septum. The rim of the access aperture then forces the periphery of the septum inwardly in the plane of the septum in a manner that is uniform radially about the entire periphery thereof.

The use of a round septum to produce uniform properties in the installed septum does, however, have drawbacks.

For example, it is desirable that a septum be so installed in the housing of a vascular access port as to present to the exterior of the vascular access port at least a minimum amount of exposed needle target area. This facilitates the locating of the septum by palpation of the skin of the patient at the implantation site of the vascular access port. It also reduces the chances that any given probe by the tip of the shaft of a hypodermic needle through the tissue of the patient at the implantation site will miss the septum entirely.

Missing the needle target area of the septum of vascular access port is a painful event for the patient. It is an event that also presents major risks. If the miss is not detected by medical personnel, the fluids in the associated hypodermic syringe could be injected subcutaneously into the pocket in which the vascular access port is implanted, producing consequences already discussed above.

A large needle target area in the septum of a vascular access port also decreases the likelihood that the desirable repeated selective penetration of the septum by the tip of a hypodermic needle will inadvertently become concentrated over time in any small region of the septum. The dispersal of puncture sites over a large needle target area slows the destructive effects of needle penetration, such as septum coring, and thus contributes to septum longevity.

Circular septums that exhibit a desired minimum amount of needle target area necessitate vascular access ports that are correspondingly large in each direction parallel to the plane of the septum. Vascular access ports of such proportion can only be implanted in correspondingly large tissue areas in the body of a patient, such as in tissue areas in the thigh or in the chest. Occasionally in robust adults, implantation in the upper arm is also a possibility.

The implantation of a vascular access port at these locations is not, however, entirely convenient for repeated ongoing therapy. At these locations, reaching the vascular access port with the tip of a hypodermic needle requires that the patient at least partially undress and remain so undressed during the entire time that the vascular access port is being involved in therapeutic activity. The implantation of vascular access ports in easily accessible portions of the human anatomy, such as in the extremities of an adult patient, would be preferable. There, a vascular access port is easy to locate by palpation and easy to access with the tip of the shaft of a hypodermic needle.

The relatively extensive dimensions of a vascular access port that uses a round septum also precludes the use of such a vascular access port with small children or with infants, as there are simply no large tissue areas in the bodies of such potential patients.

The configuration of a vascular access port to accommodate a round septum also has consequences relative to the manner in which implantation of the vascular access port must occur. Vascular access ports with round septums are correspondingly relatively extensive in each direction parallel to the plane of the septum. As a result, relatively long incisions must be made in the skin of a patient when forming the subcutaneous pocket in which the vascular access port is to be implanted. The longer the incision, the greater will be the duration of the healing process that must occur at the implantation site before therapy can commence using the vascular access port. Correspondingly, greater is the potential for infection or for other complications.

OBJECTS AND SUMMARY OF THE INVENTION

Accordingly, it is an object of the present invention to provide an improved vascular access system, and to do so in particular by providing an improved vascular access port for use in such systems.

Another object of the present invention is to provide a vascular access port that has a conventional fluid capacity, but that is capable of insertion through a small incision into a subcutaneous pocket in the body of a patient.

An additional object of the present invention is to provide a vascular access port as described above that can be implanted in smaller tissue areas in the body of an adult patient, and particularly in the extremities thereof.

A related object of the present invention is to provide a vascular access port as described above that can be used with small children and infants.

On the other hand, it is an object of the present invention to provide a vascular access port as described above, in which coring of the septum is minimized and in which an acceptably large needle target area is maintained.

Yet another object of the present invention is to provide a vascular access port that is not limited to using a circular septum in order to produce in the installed septum desired needle sealing, needle retention, and needle penetration characteristics.

Still another object of the present invention is to provide vascular access ports of the types described above in which characteristics, such as needle sealing, needle penetration, and needle retention in the installed septum, are uniform throughout the cross section of the septum.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, an implantable vascular access port is provided in which an elongated, needle-penetrable, elastomeric septum is installed in a needle-impenetrable housing. The housing is made up of a base and a cooperatively interacting cap.

The base of the housing has a floor with a continuous encircling sidewall upstanding therefrom. The sidewall terminates remote from the floor in a septum support shoulder. The space interior of the base corresponds to the fluid reservoir of the access port.

The cap of the housing has a top wall with a skirt depending therefrom. The skirt of the cap is configured to receive the end of the sidewall of the base that carries the septum support shoulder. Formed through the top wall of the cap is an access aperture that communicates with the fluid reservoir of the access port, when the sidewall of the base is received in the cap. The access aperture has an elongated outer periphery defined by a continuous encircling rim. By way of example but not limitation, the rim may be elliptical, oval, polygonal, or parabolic-ended.

Extending radially into the access aperture from the side of the rim of the access aperture adjacent to the exterior of the vascular access port is a septum retention lip. The septum retention lip assumes a parallel, spaced-apart relationship to the septum support shoulder, when the sidewall of the base is received in the cap of the housing.

A vascular access port according to the teachings of the present invention also includes a septum that is elongated in a cross section taken in the plane thereof. Thus, a septum according to the teachings of the present invention can have a periphery in the plane thereof that is, by way of example and not limitation, substantial elliptical, substantially oval, substantially polygonal, or provided with extreme ends that are substantially parabolic.

The natural configuration of a septum will be used to refer to the condition of the septum, when the septum is free of the forces that will eventually be imposed on the septum by the housing into which the septum is to be installed. The cross section of the natural configuration of the septum in the plane thereof is generally more expansive than the access aperture into which the septum becomes installed. For optimum characteristics in the installed septum, however, the periphery of the septum in the natural configuration thereof is substantially geometrically proportional to the rim of the access aperture.

Once the septum is installed in the access aperture of a housing of a vascular access port, the periphery of the septum is in a continuous sealing engagement with the rim of the access aperture. This is the installed configuration of the septum. In the installed configuration of the septum, the periphery of the septum is displaced radially inwardly in the plane of the septum relative to the natural configuration thereof by forces imposed on the periphery of the septum by the rim of the access aperture.

The periphery of the septum in the natural configuration thereof has a thickness that is greater than the distance between the septum support shoulder and the septum retention lip, when the sidewall of the base is received in the cap of the housing. The septum is disposed in the access aperture with the periphery of the septum positioned between the septum retention lip on the cap and the septum support shoulder on the base of the housing. The opposite faces of the periphery of the septum are, as a result, urged toward each other by the septum retention lip and the septum support shoulder, when the housing is assembled.

These axial forces on the periphery of the installed septum, in combination with the radially inwardly directed forces imposed by the rim of the access aperture, produce substantially uniform hydrostatic pressure in the region of the installed septum that is accessible to needle penetration during use of the implanted access port. This in turn results in substantially uniform needle sealing, needle retention, and needle penetration characteristics in the installed configuration of the septum.

A septum according to the teachings of the present invention includes an outer face on the side of the septum that is oriented toward the exterior of the housing of the vascular access port in the installed condition of the septum and an inner face on the side of the septum opposite from the outer face.

In another aspect of the present invention, support means is integrally formed with the septum for preventing buckling of the septum in the installed configuration thereof. By way of example and not limitation, such support means may comprise a needle target dome on the outer face of the septum. The target dome may be smaller in extent than the outer face of the septum. Commonly, the target dome is displaced toward the exterior of the housing of the vascular access port by forces imposed on the periphery of the septum in the installed condition thereof.

An alternate or supplementary form of a support means according to the teachings of the present invention may comprise a reinforcing plug on the inner face of the septum. The reinforcing plug may be smaller in extent than the inner face of the septum. Commonly, the reinforcing plug is displaced toward the interior of the housing of the vascular access port by forces imposed on the periphery of the septum in the installed condition thereof.

A pair of orthogonal axes can be associated with the septum in the plane thereof For convenience, these are the longitudinal axis of the septum, which is coincident with the maximum extent of the septum in the plane thereof, and the lateral axis of the septum, which is coincident with the maximum extent of the septum in the plane thereof measured perpendicular to the longitudinal axis of the septum.

The longitudinal axis of the septum intersects the periphery of the spetum at respective longitudinal extremes of the septum, and these longitudinal extremes of the septum are inwardly displaced from the natural configuration of the septum into the installed configuration of the septum by substantially equal nonzero first displacements that are directed along the longitudinal axis of the septum.

Correspondingly, the lateral axis of the septum intersects the periphery of the septum at respective medial extremes of the septum. The medial extremes of the septum are inwardly displaced from the natural configuration of the septum into the installed configuration of the septum by substantially equal nonzero second displacements that are directed along the lateral axis of the septum.

The periphery of the septum and the rim of the access aperture in which the septum is installed are so configured that the ratio of the combination of the first displacements to the distance between the longitudinal extremes of the septum in the natural configuration of the septum is equal to the ratio of the combination of the second displacements to the distance between the medial extremes of the septum in the natural configuration of the septum.

The ratio of the combination of the first displacements to the distance between the longitudinal extremes of the septum in the natural configuration thereof is, however, equal to the strain imposed along the longitudinal access of the septum in the installed configuration of the septum. Similarly, the ratio of the combination of the second displacements to the distance between the medial extremes of the septum in the natural configuration of the septum is equal to the strain along the medial axis of the septum in the installed configuration of the septum.

Therefore, in installing a septum in an access apeture according to the teachings of the present invention, the strain along the longitudinal axis of the septum is preferably equal to the strain along the lateral axis of the septum.

Alternatively, the distance between a first pair of points on the periphery of the septum that are disposed on the longitudinal axis of the septum is reduced in the installed configuration of the septum relative to the natural configuration of the septum by a first compression distance. Correspondingly, the distance between a second pair of points on the periphery of the septum disposed on the lateral axis thereof is reduced in the installed configuration relative to the natural configuration by a second compression distance.

According to teachings of the present invention, the ratio of the first compression distance to the distance between the first pair of points in the natural condition of the septum is equal to the ratio of the second compression distance to the distance between the second pair of points in the natural condition of the septum.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF EMBODIMENTS OF THE INVENTION

Figure 1:
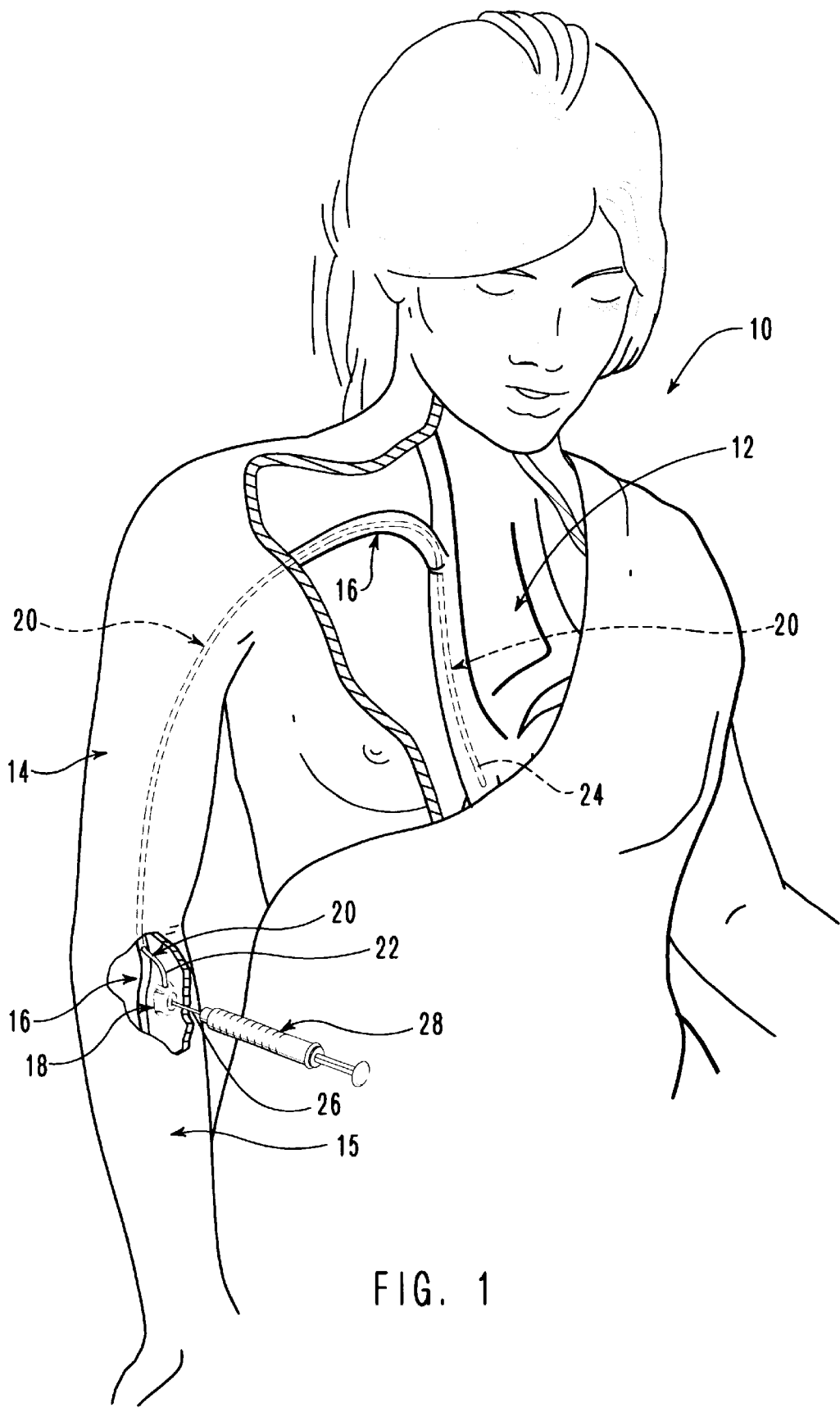
FIG. 1 is a perspective view of an implantable vascular access system including a vascular access port incorporating teachings of the present invention attached to a vascular catheter and implanted in the body of a patient.

In FIG. 1, a patient 10 is shown having a chest 12, a right arm 14, and a forearm 15 associated therewith. A vein 16 extends from forearm 15 through arm 14 and into chest 12.

Subcutaneously implanted in forearm 15 of patient 10 is one embodiment of a vascular access port 18 incorporating teachings of the present invention. Also implanted with vascular access port 18 is an elongated, pliable vascular catheter 20 that is coupled at the proximal end 22 thereof to vascular access port 18. Catheter 20 enters vein 16 in the proximity of vascular access port 18 and extends within vein 16 from forearm 15, through arm 14, and into chest 12 of patient 10. The distal end 24 of catheter 20 has been advanced through vein 16 to a desired location within chest 12 of patient 10 near the heart thereof. Distal end 24 of catheter 20 is either open, or is provided with such pressure-sensitive valving as affords for S one-way or two-way fluid flow therethrough according to the intended use of vascular access port 18 and catheter 20. The combination of vascular access port 18 and catheter 20 is, therefore, capable of functioning as a vascular access system.

By virtue of the configuration of vascular access port 18, however, that component of the vascular access system is susceptible to implantation in small tissue areas in the body of patient 10, such as in forearm 15 thereof This capability of vascular access port 18 is related not to any reduction in the overall volume occupied by vascular access port 18, but rather to the configuration of that volume in a vascular access port according to teachings of the present invention. That configuration in the vascular access port is a primary consequence of the shape of the elastomeric septum installed therein. For the same reasons, vascular access port 18 can be used as a component of a vascular access system that will benefit small children and infants.

A needle 26 of a hypodermic syringe 28 is used to deliver medication transcutaneously to the fluid reservoir in vascular access port 18. The medication flows through catheter 20 and is discharged within the body of patient 10 at distal end 24 of catheter 20. Alternatively, once the tip of needle 26 is received in the fluid reservoir of vascular access port 18, hypodermic syringe 28 can be used to aspirate bodily fluid samples from the vicinity of distal end 24 of catheter 20. These bodily fluids are drawn thereby into and through catheter 20 to the fluid reservoir in access port 18, and therefrom through needle 26 into hypodermic syringe 28.

Figure 2:
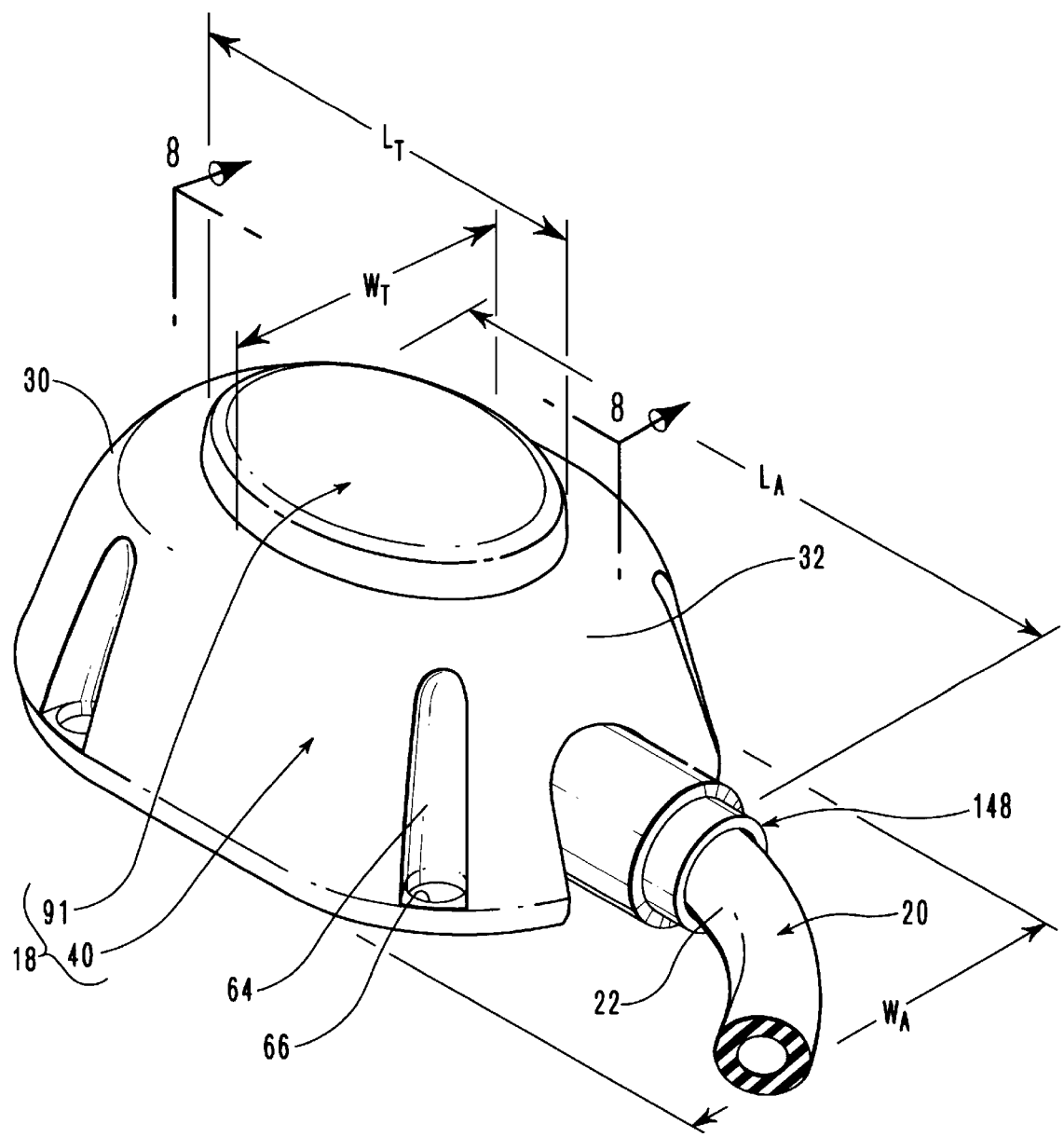
FIG. 2 is an enlarged perspective view of the vascular access port of FIG. 1 and the portion of the catheter immediately attached thereto.

As depicted in FIG. 2, vascular access port 18 includes a needle-impenetrable housing 40 that encloses a fluid reservoir not visible in FIG. 2. An elastomeric, needle-penetrable septum 91 affords for repeated selective access to the fluid reservoir in housing 40 when penetrated by the tip of the needle of a hypodermic syringe, such as hypodermic syringe 28 shown in FIG. 1.

The portion of septum 91 exposed to the exterior of vascular access port 18 is referred to as the needle target area of septum 91. As shown in FIG. 2, the needle target area of septum 91 has a maximum extent, or length $L_T$, and a width $W_T$ measured perpendicular to length $L_T$ thereof. The needle target area of septum 91, therefore, has a generally elongated configuration.

As used herein relative to any structure, the term "elongated" is intended to connote that the corresponding structure has overall dimensions measured in orthogonal directions that are unequal.

For example, as shown in FIG. 2, vascular access port 18 has a maximum extent, or length $L_A$, between a proximal end 30 and an opposed distal end 32 to which proximal end 22 of catheter 20 is attached. The length $L_A$ of vascular access port 18 between proximal end 30 and distal end 32 thereof is greater than the width $W_A$ of vascular access port 18 measured perpendicular to the length $L_A$ thereo.f Accordingly, access port 18 is also elongated within the meaning of that term intended herein.

The degree of elongation in different structures can be compared using various normalizing parameters that are derivable for a given structure from the length and width thereof.

A first such parameter is aspect ratio. The aspect ratio of a structure is the ratio of the length of the structure divided by the width of the structure. A structure that lacks elongation has a width equal to the length thereof. Thus, the aspect ratio of a structure that lacks elongation is equal to 1.00, and all elongated structures have aspect ratios that are greater than 1.00. Larger aspect ratios reflect more extreme degrees of elongation.

A second such parameter of elongation is eccentricity. The eccentricity E of an elongated structure of length L and width W is determined from the following equation:

$$E = \sqrt{1 - \left(\frac{W}{L}\right)^2} \qquad [1]$$

A structure that lacks elongation has a width W equal to the length L thereof. Thus, the eccentricity of a structure that lacks elongation is equal to zero. All elongated structures have eccentricities that are greater than zero and less than 1.00. Larger eccentricities reflect more extreme degrees of elongation.

Figure 3:
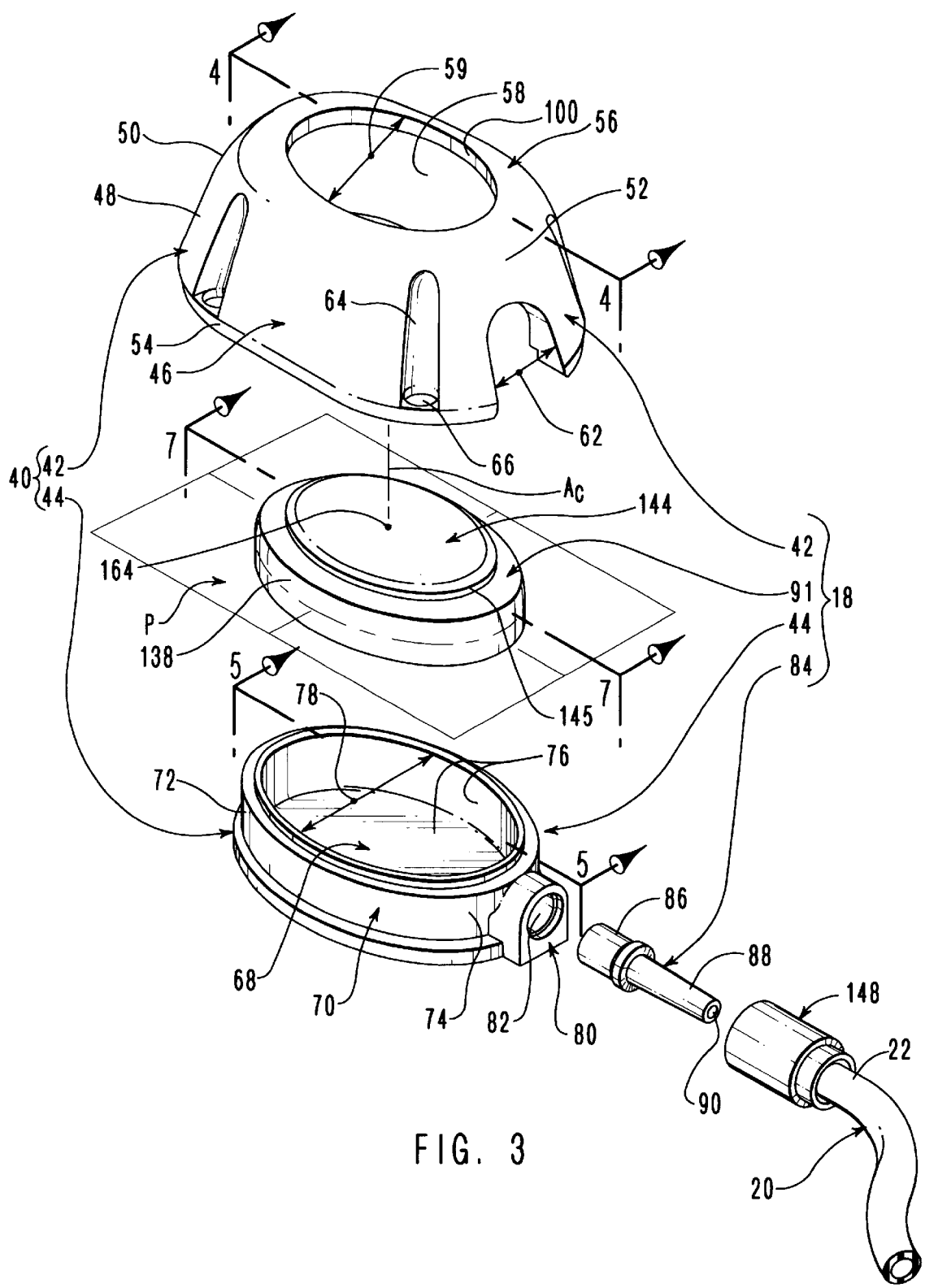
FIG. 3 is an exploded perspective view of the components.of the vascular access port of FIG. 2 with the catheter disassembled therefrom.

A better appreciation of the internal structure of vascular access port 18 can be obtained by reference to FIG. 3, which is an exploded perspective view of the elements thereof. As depicted therein, housing 40 includes an elongated cap 42 and a correspondingly elongated base 44.

Cap 42 is a cup-like structure that comprises a top wall 56 and a skirt 46 depending therefrom that terminates in a suture lip 54. As illustrated in FIG. 3, skirt 46 continuously encircles top wall 56 of cap 42. Nonetheless, appropriate discontinuous non-encircling structures attached to or depending from top wall 56 could with a complementary configuration of base 44 function with the same efficacy as does skirt 46 in vascular access port 18.

The exterior surface 48 and the interior surface 58 of cap 42 meet at suture lip 54. Interior surface 58 of cap 42 forms the walls of a receiving chamber 60 shown to best advantage in FIG. 4. Receiving chamber 60 is intended to closely nestle base 44, the other component of housing 40, in the manner illustrated in FIG. 6. Receiving chamber 60 opens outwardly for that purpose to the exterior of cap 42 at a housing assembly entrance 61 that is also shown to best advantage in FIG. 4. Assembly entrance 61 is substantially encircled by suture lip 54. An elongated target aperture 59 is formed through top wall 56 of cap 42 to receiving chamber 60.

Cap 42 has a proximal end 50 and an opposed distal end 52 at which a U-shaped stem slot 62 is formed through suture lip 54 and skirt 46. A plurality of circumferentially spaced suture channels 64 in exterior surface 48 of cap 42 extends from top wall 56 to suture lip 54. There, suture lip 54 is provided in each instance with a respective suture hole 66. Suture holes 66 are used to secure vascular access port 18 in a subcutaneous implantation pocket.

Figure 5:
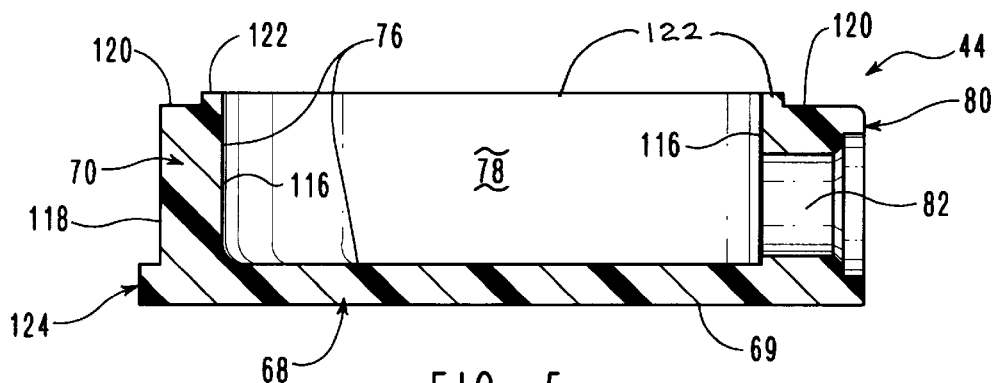
FIG. 5 is a cross-sectional elevation view of the base of FIG. 3 taken along section line 5—5 shown therein.

Base 44 of housing 40 includes a floor 68 and a continuous-encircling sidewall 70 upstanding therefrom. As understood with enhanced clarity by reference to FIG. 5, the interior surface 76 of base 44 includes the floor and the walls of a fluid reservoir 78 of vascular access port 18 that is formed interior of base 44. Base 44 has a proximal end 72 and a distal end 74 from which projects a stem housing 80 of U-shaped cross section. As best seen in FIG. 5, a passageway 82 extends longitudinally through stem housing 80 to fluid reservoir 78. Stem housing 80 is received in stem slot 62 of cap 42, when sidewall 70 of base 44 is nestled in receiving chamber 60 of cap 42 in the manner shown in FIG. 6.

Vascular access port 18 also includes a substantially cylindrical outlet stem 84 shown in perspective in FIG. 3 as including a proximal end 86 that is configured to be received within passageway 82 in stem housing 80. The distal end 88 of outlet stem 84 is used to couple vascular access port 18 with catheter 20. It is possible, by contrast, to manufacture base 44 of housing 40 with an outlet stem, such as outlet stem 84, that is integrally formed therewith. A passageway 90 extends longitudinally through outlet stem 84 from proximal end 86 to distal end 88 thereof As a result, passageway 90 communicates with fluid reservoir 78 when proximal end 86 of outlet stem 84 is received in passageway 82 of stem housing 80. Such a view of the structures described can best be derived from FIG. 8.

Receiving chamber 60 in cap 42 is so configured as to enclose the end of sidewall 70 of base 44 remote from floor 68 thereof. In assembling cap 42 and base 44 in this manner, base 44 enters receiving chamber 60 through assembly entrance 61 and advances thereinto until suture lip 54 on cap 42 is flush with the outer surface 69 of floor 68 of base 44. Stem housing 80 is received in stem slot 62, so that outlet stem 84 projects outwardly from the assembly. Target aperture 59 then affords communication between the exterior of housing 40 and fluid reservoir 78 therein.

Cap 42, base 44, and outlet stem 84 can each be made from a medical grade plastic. In the alternative, each can be manufactured from other needle-impenetrable materials, such as metals, ceramics, or composites. Cap 42, base 44, and stem 84 can individually be made from different materials, if desired.

FIG. 3 also depicts the final component of vascular access port 18, an elastomeric needle-penetrable septum 91. As depicted in FIG. 3, septum 91 is an elongated, substantially planar structure with an outer periphery 138. In a cross section of septum 91 taken in the plane P thereof, periphery 138 of septum 91 is substantially elliptical. Nonetheless, other configurations for the periphery of an elongated septum, such as septum 91, are within the scope of the present invention and will be discussed relative to subsequent figures. Septum 91 has a central axis $A_c$ that is perpendicular to plane P and passes through the center 164 of the top surface of septum 91.

When installed in vascular access port 18, septum 91 is positioned between base 44 and cap 42. As a result, septum 91 seals target aperture 59, but septum 91 nonetheless also enables repeated selective access to fluid reservoir 78 by the tip of the shaft of a hypodermic needle that is penetratingly advanced through septum 91.

Septum 91 is made from a medical grade silicone or other comparable materials having a Shore "A" durometer in a range from about 25 to about 85. More preferably, the Shore "A" durometer of the material of septum 91 is in a range from about 35 to about 75, and most preferably in a range from about 45 to about 65.

The internal features of the components of housing 44 will be discussed in greater detail below.

Figure 4:
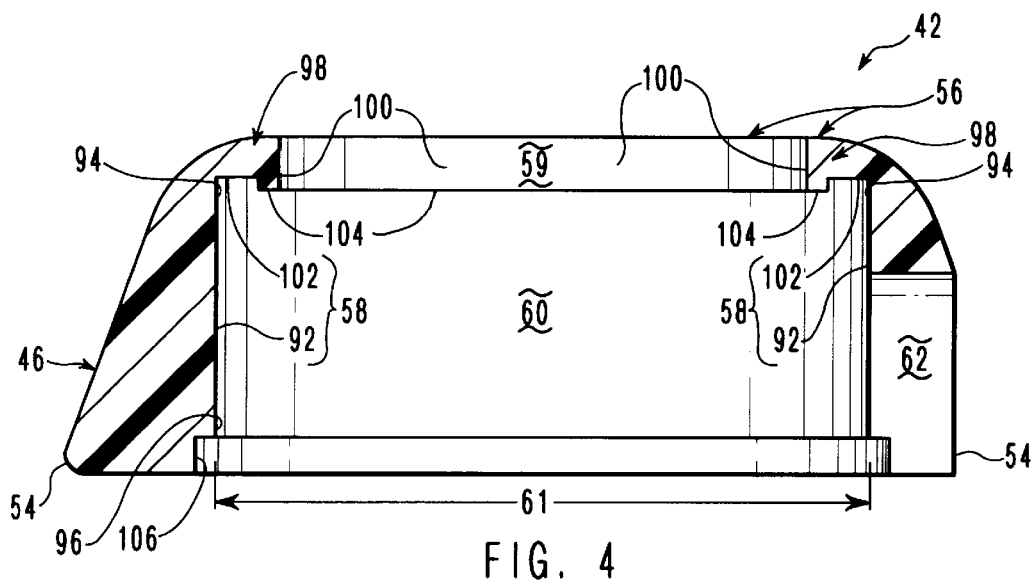
FIG. 4 is a cross-sectional elevation view of the cap of FIG. 3 taken along section line 4—4 shown therein.

As depicted in FIG. 4, skirt 46 of cap 42 has an inner surface 92 that extends between an upper end 94 and a lower end 96 thereof Except at stem slot 62 formed therethrough, skirt 46 encircles receiving chamber 60. Formed in lower end 96 of skirt 46 is an alignment notch 106. Alignment notch 106 is substantially continuous in the embodiment illustrated, being interrupted by stem slot 62, but alignment notch 106 may be configured otherwise, provided that corresponding structures on base 44 are appropriately modified in a complementary manner.

Radially inwardly projecting from inner surface 92 at upper end 94 thereof is a continuous septum retention lip 98. Septum retention lip 98 terminates at a free inner surface 100 that encircles target aperture 59 in a continuous manner.

Extending between inner surface 92 of skirt 46 and inner surface 100 of septum retention lip 98 is a bearing surface 102 that is continuous in the embodiment illustrated. A first gripping ridge 104 projects from bearing surface 102 normal thereto at a location adjacent to inner surface 100 of septum retention lip 98. First gripping ridge 104 is continuous in the embodiment of vascular access port 18 illustrated.

As depicted in FIG. 5, sidewall 70 of base 44 has an outer surface 118 and an inner surface 116 that encircles fluid reservoir 78. Extending radially outward from outer surface 118 of sidewall 70 at floor 68 is an alignment shoulder 124 that is substantially continuous in the embodiment illustrated, being interrupted by stem housing 80. Alignment shoulder 124 may be configured otherwise, provided that corresponding structures on cap 42 are appropriately modified in a complementary manner.

Sidewall 70 of base 44 extends from floor 68 to a free septum support shoulder 120 that is continuous in the embodiment illustrated. Upstanding from septum support shoulder 120 adjacent to inner surface 116 of sidewall 70 is a second gripping ridge 122 that is also continuous in the embodiment illustrated.

Figure 6:
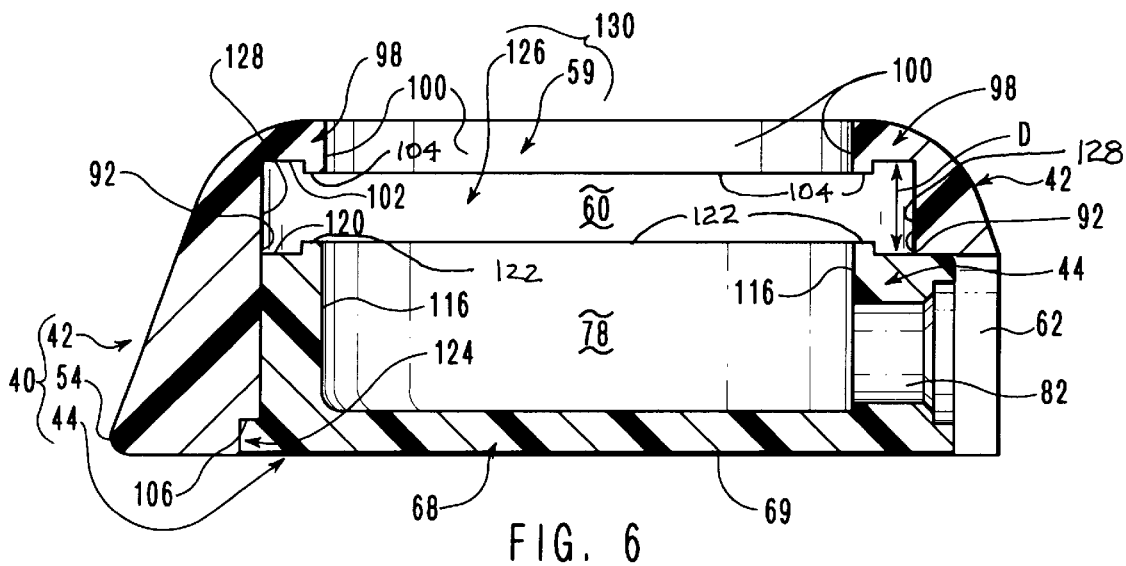
FIG. 6 is a cross-sectional elevation view of the base of FIG. 5 received in the cap of FIG. 4.

FIG. 6 depicts the relationship among the structures of cap 42 and base 44, when base 44 is received in cap 42. Sidewall 70 of base 44 is configured to fit tightly within receiving chamber 60 of cap 42 with alignment shoulder 124 on base 44 fitting into alignment notch 106 on cap 42. Bearing surface 102 of septum retention lip 98 is, as a result, positioned in parallel spaced-apart relationship to septum support shoulder 120, separated therefrom by a distance D.

The portion of receiving chamber 60 not filled in this manner by base 44 and not intended to function as part of fluid reservoir 78 comes instead to perform as a septum receiving aperture 126. The portion of inner surface 92 of skirt 46 of cap 42 above septum support shoulder 120 correspondingly comes to function as a continuous rim 128 of septum receiving aperture 126. Rim 128 of septum receiving aperture 126 is elongated in shape, and in the embodiment illustrated in harmony with the cross-section of periphery 138 of septum 91 is substantially elliptical. Nonetheless, other configurations for rim 128 of septum receiving aperture 126 are within the scope of the present invention. By way of example and not limitation, rim 128 may thus be elliptical, oval, polygonal, or parabolic-ended.

With base 44 assembled in cap 42, target aperture 59 communicates between the exterior of housing 40 and one side of septum receiving aperture 126. The opposite side of septum receiving aperture 126 communicates with fluid reservoir 78. Thus, target aperture 59 and septum receiving aperture 126 together function as an access aperture 130 through which fluid reservoir 78 communicates with the exterior of housing 40.

Generally, the periphery of an elongated septum, such as septum 91, is geometrically proportional to, but larger than, the shape of the rim of the access aperture of the vascular access port in which the septum is to be installed. The ramifications of this feature of septum 91 on the interactions of the elements of housing 40 with septum 91 is investigated in substantial detail in due course.

Figure 7:
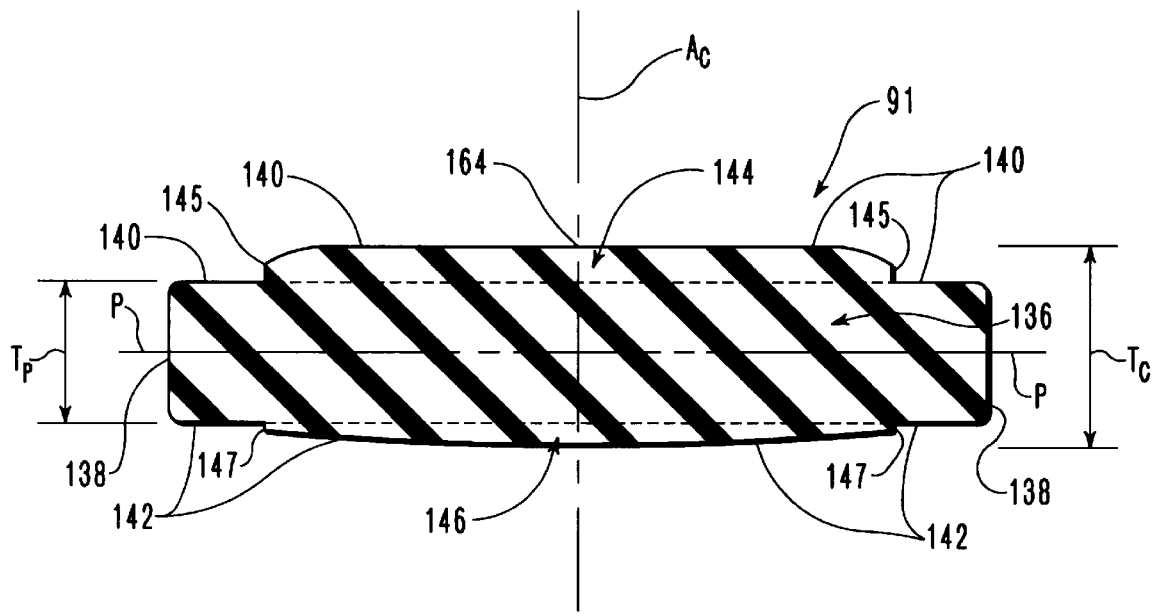
FIG. 7 is a cross-sectional elevation view of the natural configuration of the uninstalled septum of FIG. 3 taken along section line 7-7 shown therein, which coincides with the longitudinal axis of the septum.

A cross-sectional elevation view of septum 91 in the natural configuration thereof, free of external forces, is shown in FIG. 7. There, septum 91 can be seen to include a septum body 136 having an outer face 140 on the side of septum 91 that is oriented to the exterior of housing 40 when septum 91 is installed therein. Correspondingly, septum body 136 has an inner face 142 on the opposite side of septum 91 from outer face 140 thereof.

At periphery 138, septum body 136 assumes a minimum thickness $T_p$ between outer face 140 and inner face 142. About central axis $A_c$ of septum 91, however, the central thickness $T_c$ of septum body 136 is a maximum, greater than minimum thickness $T_p$ at periphery 138 thereof. The increase in thickness of septum body 136 toward center 164 of septum 91 is a result of the formation of structures at outer face 140 and inner face 142, respectively.

Radially inwardly from periphery 138 of septum 91, outer face 140 of septum body 136 bulges laterally outwardly from septum body 136 to form a needle target dome 144. Accordingly, needle target dome 144 is smaller in extent than is outer face 140 of septum body 136.

As best appreciated in FIG. 3, needle target dome 144 is enclosed within a boundary 145 that is elongated. When septum 91 is assembled in housing 40 in the manner of FIG. 2, it is the portion of outer face 140 of septum body 136 within boundary 145 of needle target dome 144 that is exposed to the exterior of access port 18 through target aperture 59. Thus, in the embodiment of vascular access port 18 illustrated, the surface of needle target dome 144 is substantially coincident with the needle target area of septum 91.

In most instances, it can be anticipated that boundary 145 of needle target dome 144 will coincide substantially with inner surface 100 of septum retention lip 98. Nonetheless, within the scope of the teachings of the present invention, this relationship need not necessarily always exist. Furthermore, while boundary 145 of needle target dome 144 may appear in FIG. 3 to be similar in shape to periphery 138 of septum 91, this relationship also need not necessarily be maintained according to the teachings of the present invention.

Radially inwardly from periphery 138 of septum 91, inner face 142 of septum body 136 bulges laterally outwardly from septum body 136 to form a reinforcing plug 146. Accordingly, reinforcing plug 146 is smaller in extent than is inner face 142 of septum body 136.

As best appreciated in FIG. 7, reinforcing plug 146 is enclosed within a boundary 147 that is elongated much in the manner of boundary 145 of needle target dome 144. When septum 91 is assembled in housing 40, it is the portion of inner face 142 within boundary 147 of reinforcing plug 146 that is exposed to fluid reservoir 78 on the interior of vascular access port 18.

In most instances, it will be desirable that boundary 147 of reinforcing plug 146 engages inner surface 116 of sidewall 70 of base 44. Under those circumstances, boundary 147 of reinforcing plug 146 will assume substantially the same shape as the cross section of fluid reservoir 78 taken in a plane parallel to floor 68 of base 44. Nonetheless, within the scope of the teachings of the present invention, this relationship need not necessarily always exist. Furthermore, while boundary 147 of reinforcing plug 146 may be similar in shape to periphery 138 of septum 91, this relationship also need not necessarily be maintained according to the teachings of the present invention.

In FIG. 7, boundary 145 of needle target dome 144 precisely overlies boundary 147 of reinforcing plug 146. This is a result of structural relationships existing among the needle-impenetrable elements of housing 40.

First, as illustrated best in FIG. 6, inner surface 100 of septum retention lip 98 on cap 42 is of the same size and shape as inner surface 116 of sidewall 70 of base 44. Therefore, target aperture 59, which is bounded by inner surface 100 of septum retention lip 98, corresponds in size and shape to the cross section of fluid reservoir 78 that is bounded by inner surface 116 of sidewall 70 of base 44.

Second, when base 44 is received in cap 42, in the manner illustrated in FIG. 6, inner surface 100 of septum retention lip 98 comes to be disposed in precise alignment with and above inner surface 116 of sidewall 70 of base 44. Thus, target aperture 59 overlies fluid reservoir 78 when the components of housing 40 have become assembled.

Although these relationships among the elements of housing 40 of vascular access port 18 have demonstrated effectiveness, those relationships need not necessarily be precisely replicated in an access port embodying teachings of the present invention.

Access port 18 is assembled by initially positioning septum 91 within cap 42 such that needle target dome 144 is received within target aperture 59. The portion of outer face 140 of septum body 136 that is radially outside of boundary 145 of needle target dome 144 comes as a result to rest against bearing surface 102 on septum retention lip 98. Base 44 is then inserted into cap 42, sandwiching septum 91 therebetween. Septum support shoulder 120 is urged against the portion of inner face 142 of septum body 136 that is radially outside of boundary 147 of reinforcing plug 146. This seals access to fluid reservoir 78 through target aperture 59. The result is shown in cross section in FIG. 8, which depicts the installed configuration of septum 91.

Cap 42 is secured to base 44 by ultrasonically welding alignment shoulder 124 of base 44 in alignment notch 106 of cap 42. In the alternative, various medical grade adhesives or conventional mechanical connections can be used to secure cap 42 and base 44. Ultrasonic welding or a medical grade adhesive is also used to secure proximal end 86 of stem 84 in passageway 82 of stem housing 80.

Housing 40 interacts with the installed configuration of elongated septum 91 to produce substantially uniform stress in septum 91 in plane P thereof. Substantially uniform stress of this type in the installed configuration of septum 91 results in uniform needle sealing, needle penetration, and needle retention characteristics throughout the entire cross section of septum 91. Needle coring in septum 91 is minimized by adjusting to within acceptable bounds the degree of uniform stress of this type produced in the installed configuration of septum 91. These effects of the interaction of housing 40 on septum 91 will be explored in detail in due course.

Catheter 20 is coupled to stem 84 by sliding proximal end 22 of catheter 20 over free distal end 88 of stem 84. A cylindrical locking sleeve 148 is then advanced along catheter 20 toward and into abutment against vascular access port 18.

To implant vascular access port 18, a subcutaneous pocket is first created in which to receive vascular access port 18. For this purpose an incision is made in the skin of patient 10 at the intended implantation site, and a pocket is enlarged therethrough below the skin. Vascular access port 18 is inserted through the incision into the subcutaneous pocket and is secured therein as desired using suture holes 66.

Outlet stem 84, which is positioned at distal end 74 of base 44 in alignment with the longitudinal axis of housing 40, enters into the subcutaneous pocket last, following the balance of vascular access port 18. By so doing, vascular access port 18 can be secured in the subcutaneous pocket before medical personnel are required to attend to the implantation of vascular catheter 20. Catheter 20 may even be coupled to outlet stem 84 of vascular access port 18 after access port 18 has been entered into and secured within the subcutaneous implantation pocket.

The positioning of outlet stem 84 on an extreme end of housing 40 allows the incision made in the skin of patient 10 to be only so long as will accommodate the width $W_A$, rather than the length $L_A$, of vascular access port 18. The elongation of vascular access port 18 thus reduces the length of the incision required for the implantation thereof. The elongation in vascular access port 18 is facilitated in largest measure by the elongation of septum 91 that is installed therein.

In one aspect of the present invention, access means are provided in housing 40 for permitting select fluid communication through septum 91 with fluid reservoir 78 by the tip of the needle of a hypodermic syringe and for producing substantially uniform stress in septum 91 in the installed configuration thereof. By way of example and not limitation, one embodiment of such an access means according to the teachings of the present invention includes access aperture 130 shown to best advantage in FIG. 6. With septum 91 disposed in access aperture 130 as in FIG. 8, selected fluid communication can be effected at will with fluid reservoir 78 only by passing through septum 91 the tip of the needle of a hypodermic syringe, such as hypodermic syringe 28 shown in FIG. 1.

The interaction between access aperture 130 and septum 91 also produces substantially uniform hydrostatic pressure in the portion of septum 91 accessible to probing by needle 26 in the installed configuration of septum 91. This in turn results in substantially uniform needle penetration force and needle retention force in that portion of septum 91.

Accordingly, in one aspect of an access means according to the teachings of the present invention, constriction means are provided for displacing periphery 138 of septum 91 radially inwardly in plane P of septum 91. By way of example and not limitation, one embodiment of such constriction means comprises a rim, such as rim 128 of access aperture 130, which has a shape in the plane thereof that is geometrically proportional to but smaller than, the cross section of periphery 138 of septum 91 in the plane P thereof. When septum 91 is disposed in an access aperture configured in this manner, rim 128 radially inwardly displaces periphery 138 of septum 91 in the plane thereof in such a manner as has been found to produce substantially uniform hydrostatic pressure in the portion of septum 91 accessible to needle penetration.

Figure 9:
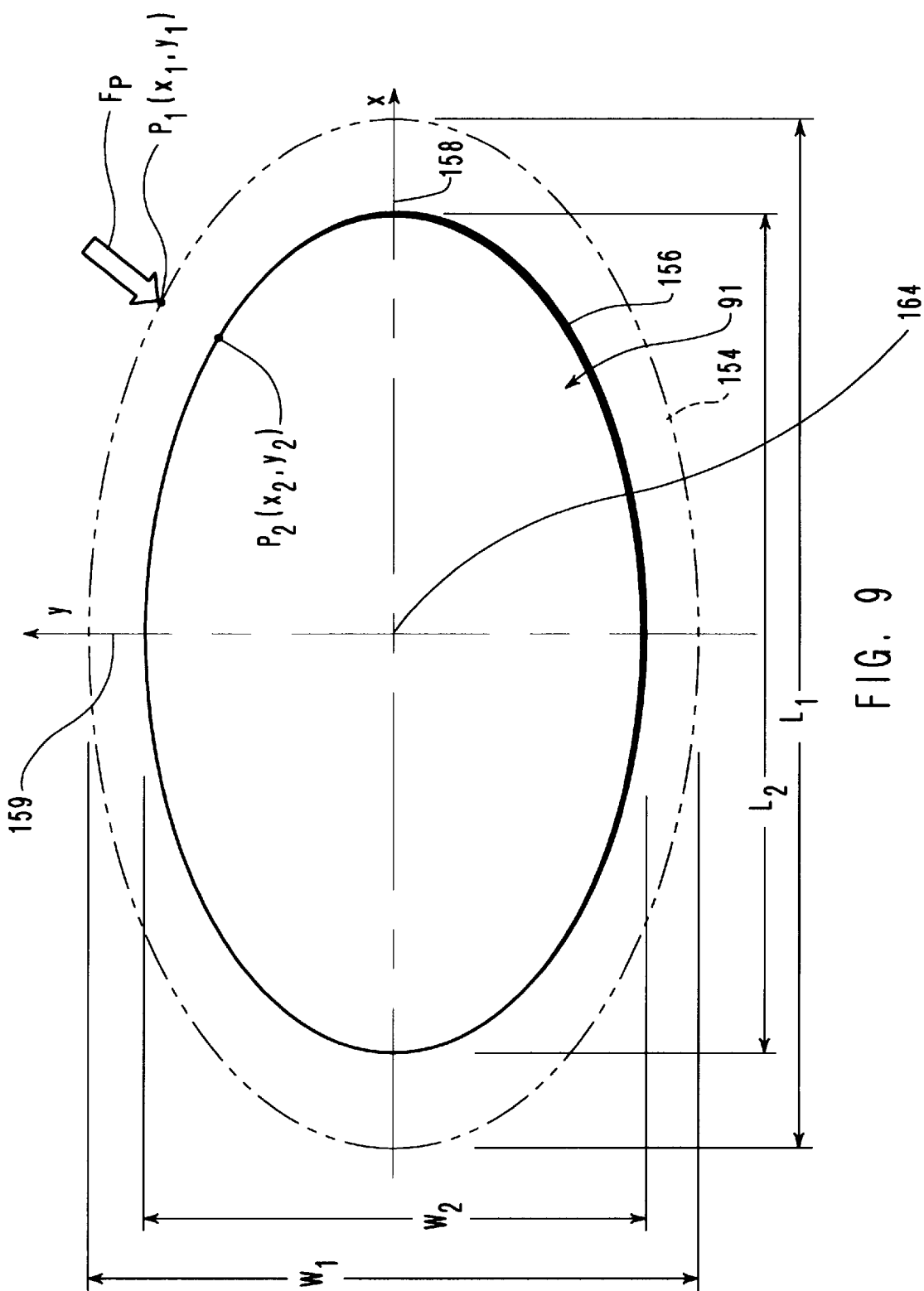
FIG. 9 is a diagram that contains comparative plan views superimposed on a common coordinate axis of a septum incorporating teachings of the present invention, first in a natural condition thereof free of externally imposed forces and shown in phantom, and second in an installed condition thereof shown in solid line with the outer periphery displaced radially inwardly, as when disposed in the vascular access port in FIGS. 2 and 8.

The diagram in FIG. 9 will be used for illustrating the relative configuring of access aperture 130 and septum 91 utilized toward that end.

In FIG. 9, a natural configuration periphery 154 of septum 91 is shown in phantom, which corresponds to the profile of the periphery of septum 91 prior to being disposed in access aperture 130 of housing 40. By way of comparison, also shown in FIG. 9, but in solid line, is an installed configuration periphery 156 of septum 91 illustrating the size of the periphery of septum 91 once septum 91 is positioned within access aperture 130 of housing 40.

Superimposed on natural configuration periphery 154 and installed configuration periphery 156 in FIG. 9 is a coordinate axis. For convenience, the origin of the coordinate axis coincides with center 164 of septum 91 in both the natural configuration and the installed configuration thereof. The first of the axes of the coordinate axis is an X-axis that is coincident with the maximum extent of septum 91 and therefore with the longitudinal axis 158 thereof in both the natural configuration and the installed configuration. Therefore, the X-axis and longitudinal axis 158 intersect natural configuration periphery 154 of septum 91 at natural longitudinal extremities 107, 108. Correspondingly, the X-axis and longitudinal axis 158 intersect installed configuration periphery 156 of septum 91 at respective installed longitudinal extremes 109, 110. Longitudinal extremes 109, 110, are translated inwardly toward center 164 of septum 91 from natural longitudinal extremities 107, 108, by substantially nonzero equal displacements $M_1$ and $M_2$ respectively. The second of the axes of the coordinate axis is a Y-axis that is coincident with the maximum extent of septum 91 measured perpendicular to longitudinal axis 158. Therefore, the Y-axis of the coordinate axes in FIG. 9 is coincident with the lateral axis 159 of septum 91 in the natural configuration and in the installed configuration thereof. Therefore, the Y-axis and lateral axis 159 intersect natural configuration periphery 154 of septum 91 at natural medial extremes 111, 112. Correspondingly, the Y-axis and lateral axis 159 intersect installed configuration periphery 156 of septum 91 at respective installed medial extremes 113, 114. Medial extremes 113, 114, are translated inwardly toward center 164 of septum 91 from natural medial extremes 111, 112, by substantially equal nonzero second displacements $N_1$ and $N_2$ respectively. As illustrated in FIG. 9, the natural configuration of septum 91 has a natural configuration periphery 154 with a maximum extent or length $L_1$ that is reduced in the installed configuration of septum 91 to an installed configuration periphery 156 having a maximum extent or length $L_2$. Length $L_2$ of installed configuration periphery 56 is thus shorter than length $L_1$ of natural configuration periphery 154 by an amount equal to the combination of first displacements $M_1$ and $M_2$. Thus:

$$L_1 - L_2 = M_1 + M_2. \qquad [1A]$$

In an orthogonal direction, septum 91 in the natural configuration thereof has a natural configuration periphery 154 with a maximum extent measured perpendicular to longitudinal axis 158 that is equal to a width $W_1$. This dimension of septum 91 decreases in the installed configuration thereof to produce an installed configuration periphery 156 having a corresponding width $W_2$. Width $W_2$ of installed configuration periphery 156 is thus shorter than width $W_1$ of natural configuration periphery 154 by an amount equal to the combination of second displacements $N_1$ and $N_2$. Thus:

$$W_1 - W_2 = N_1 + N_2. \quad [1B]$$

A point $P_1(x_1, y_1)$ on natural configuration periphery 154 of septum 91 is illustrated, only by way of example, in the first quadrant of the overlying coordinate axis shown. Septum 91 is disposed in access aperture 130 so configured as to produce substantially uniform hydrostatic pressure in the portion of septum 91 subjected to needle penetration. In assuming this installed condition in access aperture 130, rim 128 of access aperture 130 imposes upon each point on natural configuration periphery 154 of septum 91 a force that is radially inwardly directed. The force $F_p$ shown in FIG. 9 represents the force of this type applied by rim 128 of access aperture 130 to point $P_1$ on natural configuration periphery 154.

As a result of the imposition of said such forces, each point on natural configuration periphery 154 of septum 91 is displaced radially inwardly. With center 164 of septum 91 remaining fixed at the origin of the overlying coordinate axis shown, under the influence of force $F_p$, point $P_1$ on natural configuration periphery 154 of septum 91 assumes a new location on installed configuration periphery 156 at point $P_2(x_2, y_2)$. Point $P_2(x_2, y_2)$ on installed configuration periphery 156 of septum 91, is also in effect on rim 128 of access aperture 130 as well. This is due to the sealing engagement effected by installed configuration periphery 156 of septum 91 with rim 128 of access aperture 130.

It is intended according to the teachings of the present invention to so configure rim 128 of access aperture 130 and periphery 138 of septum 91 that, in the installed configuration of septum 91, a compressive strain $\epsilon_x$ is produced in septum 91 along longitudinal axis 158 of septum 91 that is equal to a compressive strain $\epsilon_y$ produced in septum 91 along lateral axis 159 thereof. Thus, in the installed configuration of the septum:

$$\epsilon_x = \epsilon_y. \quad [2]$$

Utilizing the terms illustrated in FIG. 9, and Equation No. 1A the change in length of the natural configuration of septum 91 along longitudinal axis 158 thereof in assuming the installed configuration of septum 91 is a first compression distance $C_x$ calculated as follows:

$$C_x = L_2 - L_1 = M_1 + M_2. \quad [3]$$

Similarly, using Equation No. 1B the change in width of the natural configuration of septum 91 along lateral axis 159 in assuming the installed configuration of septum 91 is equal to a second compression distance $C_y$ calculated as follows:

$$C_y = W_2 - W_1 = N_1 + N_2. \quad [4]$$

The strain imposed on an article is equal to the ratio of the change in length or width of that article to the original length or width, respectively, thereof. Therefore, the ratio of first compression distance $C_x$ to the maximum extent or length $L_1$ of septum 91 in the natural configuration thereof is equal to the ratio of second compression distance $C_y$ to width $W_1$ of septum 91 in the natural configuration thereof. Substituting Equation Nos. 3 and 4 above into Equation No. 2 produces the following relationships:

$$\frac{L_1 - L_2}{L_1} = \frac{W_1 - W_2}{W_1} \text{ and;} \quad [5]$$

$$\frac{M_1 + M_2}{L_1} = \frac{N_1 + N_2}{W_1} \quad [5A]$$

Alternatively, with center 164 of septum 91 remaining fixed at the origin of the overlying coordinate axis shown, the longitudinal extremes of septum 91 are each displaced from the natural configuration thereof into the installed configuration thereof by substantially equal nonzero first displacements $M_1$ and $M_2$ along longitudinal axis 158 of septum 91. Correspondingly, the medial extremes of septum 91 are displaced inwardly from the natural configuration thereof into the installed configuration thereof by substantially equal nonzero second displacements $N_1$ and $N_2$ directed along lateral axis 159 of septum 91. In these terms, Equation as a consequence of No. 2; Equation Nos. 5 and 5A stipulate that the ratio of the combination of the first displacements to the distance between the longitudinal extremes of septum 91 in the natural configuration thereof is equal to the ratio of the combination of the second displacements to the distance between said medial extremes of septum 91 in said natural configuration thereof One approach to achieving the condition set forth in Equation No. 2 along both the longitudinal axis and the lateral axis of septum 91 is to configure rim 128 of access aperture 130 to be both smaller than the natural configuration of septum 91 and geometrically proportional to periphery 138 thereof.

The efficacy of this design relationship has been verified through empirical studies.

An embodiment of a septum, such as septum 91, and a corresponding access aperture 130 with a rim 128 conforming to the above teachings each had elliptical configurations and the following dimensions identified by the corresponding reference characters in FIG. 9.

Septum:
$L_1$=0.68 inches
$W_1$=0.47 inches $$\text{Aspect ratio} = \frac{L_1}{W_1} = 1.45$$

$$E = \sqrt{1 - \left(\frac{W_1}{L_1}\right)^2} = 0.72$$

Access aperture:
$L_2$=0.64 inches
$W_2$=0.44 inches $$\text{Aspect ratio} = \frac{L_2}{W_2} = 1.45$$

$$E = \sqrt{1 - \left(\frac{W_2}{L_2}\right)^2} = 0.725$$

As septum 91 and access aperture 130 were both elliptical and possessed of equivalent aspect ratios and eccentricities, septum 91 and access aperture 130 were geometrically proportional.

It should be noted, however, that aperture 130 was not simply smaller in each direction of measure than septum 91 by some fixed increment. This is most readily apparent when the difference in size between septum 91 and access aperture 130 is compared along orthogonal directions of measure taken respectively parallel to longitudinal axis 158 of septum 91 and lateral axis 159 of septum 91. Along longitudinal axis 158, the difference in size between septum 91 and access aperture 130 was the following:

$$L_1-L_2=0.040 \text{ inches.}$$

On the other hand, the difference in size between septum 91 and access aperture 130 along lateral axis 159 was the following:

$$W_1-W_2=0.030 \text{ inches.}$$

Computerized modeling of the installation according to the teachings of the present invention of a septum, such as septum 91 dimensioned as indicated above, in an access aperture, such as access aperture 130 dimensioned as indicated above, has provided insights relative to the internal stresses developed in an installed configuration of such a septum. Of primary concern was to quantify a physical parameter at each location throughout the needle penetration region of the installed configuration that would correlate in some way to needle penetration force and needle retention force at that location.

Needle penetration force in any given instance is dependent upon a number of properties of the needle being utilized and the material of the septum being penetrated. For example, the resistance to needle penetration is proportional to needle size, the internal cohesion of septum material resisting separation at the tip of an advancing needle, and the frictional drag forces that arise between the exterior of the needle and the septum material along the path of needle penetration. Those frictional drag forces naturally increase as the path of needle penetration lengthens during the advancement of a needle from the exterior of a septum through the septum body to the fluid reservoir within the housing in which the septum is installed.

Nonetheless, these factors are in a relative sense substantially invariant for any given needle and any given septum, changing little as a result of the forces imposed on the septum by the housing in which the septum is installed. Thus, these factors bear only marginally on the stability of the installed septum in a housing, on the ability of the material of the septum to seal about the exterior of a penetrating needle during the presence of the shaft of the needle in the path of needle penetration, or on the effectiveness of the material of the septum to seal the path of needle penetration once the shaft of the needle has been withdrawn.

Medical grade silicone is, for all practical purposes, an incompressible fluid-like material that responds to externally-imposed forces by distorting freely, equilibrating the internal pressure and shear strains produced by those forces and the resulting deformation. Thus, the internal stress state of an installed silicone septum is characterizable by a physical parameter referred to as hydrostatic pressure. In studying the distribution of hydrostatic pressure in the installed configuration of septum 91, finite element analysis techniques were used.

The first step in that process involved the development in computer software of a virtual septum of the size and shape of septum 91. The virtual septum was then subdivided mathematically into a large plurality of minute abutting block elements, each defined by six (6) flat faces intersecting in eight (8) linear edges that each terminate between a pair of eight (8) corners. The block elements provided the best tradeoff between numerical accuracy and computational efficiency in conducting a finite element analysis of the behavior of the overall structure of the virtual septum under externally imposed forces. Care was taken in planning the block elements to avoid the creation of extremely irregular shapes.

Figure 10:
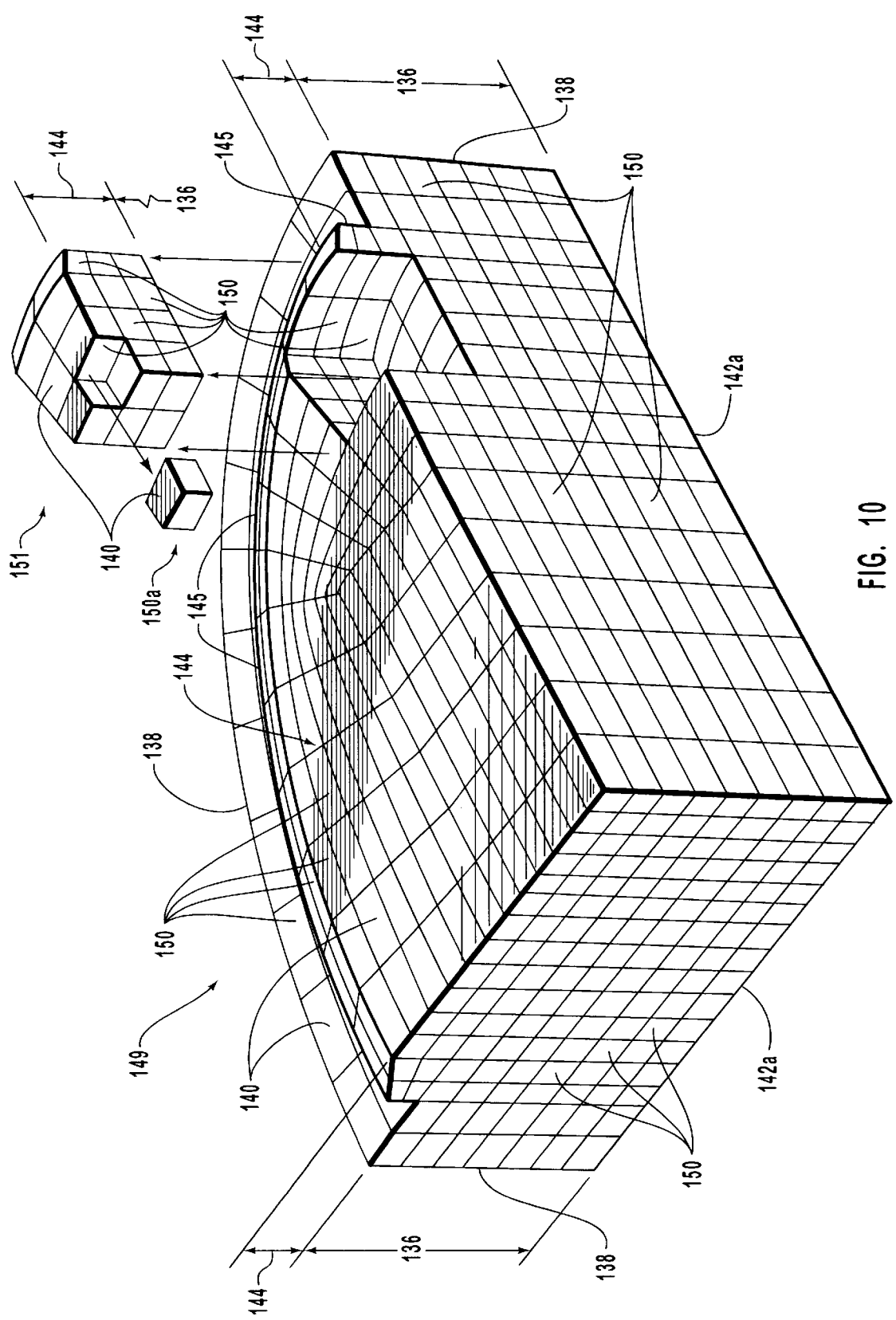
FIG. 10 is a perspective view of a quadrant of a virtual septum incorporating teachings of the present invention in the natural configuration thereof overlaid by a finite element mesh.

This approach to the study conducted is illustrated in FIG. 10. There, a quadrant of a virtual septum 149 is illustrated overlain by a finite element mesh grid that resulted from the mathematical subdivision of virtual septum 149 into a plurality of block elements 150. A subset 151 of adjacent block elements 150 is shown displaced out of the finite element mesh grid, above outer face 140 of septum body 136 of virtual septum 149 near boundary 145 of needle target dome 144. Additionally, a single block structure 150a is shown displaced laterally from the position thereof in subset 151. For simplicity, virtual septum 149 included no reinforcing plug 146 of the type illustrated in FIG. 7. Thus, while outer face 140 of virtual septum 149 conforms closely in shape and size to outer face 140 of septum 91, inner face 142a of septum body 136 of virtual septum 149 is planar within periphery 138.

The material response parameters of the silicone material of septum 91 were then determined empirically and fitted by a non-linear regression process to an appropriate mathematical representation. This mathematical representation of the material response parameters of the material of septum 91 were then added to the software depicting virtual septum 149. A condition of incompressible material behavior was imposed on the material of virtual septum 149 by the computer software.

Next, rigid virtual housing surfaces representing the surfaces of cap 42 and base 44 that define access aperture 130 were also programmed into the computer software. Such virtual housing surfaces included bearing surface 102 and inner surface 92 of cap 46, as well as septum support shoulder 120 on base 44. For simplicity, first gripping ridge 104 on bearing surface 102 and second gripping ridge 122 on septum support shoulder 120 were omitted.

Figure 11:
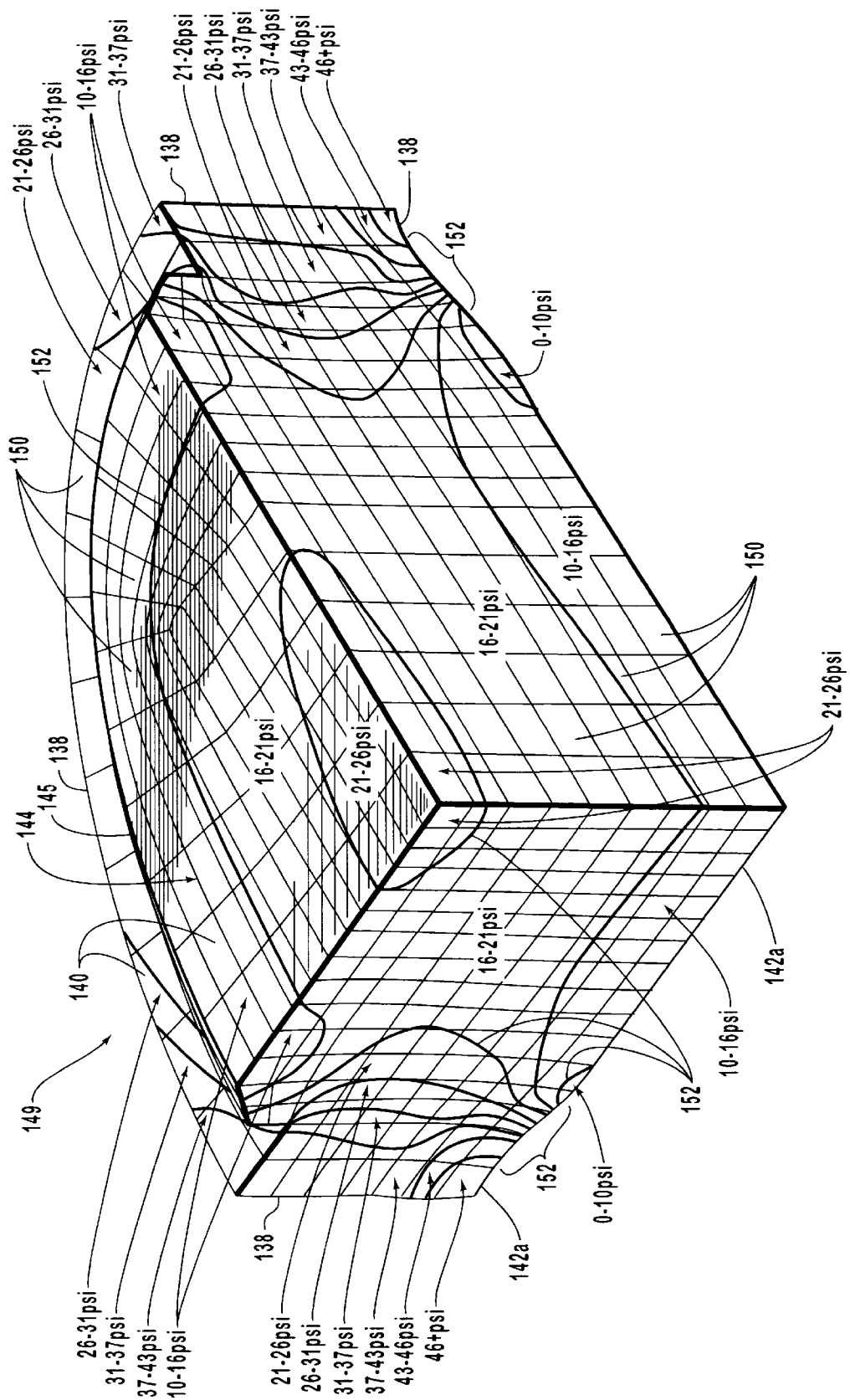
FIG. 11 is a perspective view of the quadrant of the virtual septum and associated finite element mesh of FIG. 10 showing gradients of hydrostatic pressure produced therein by the application along the longitudinal and laterial; and axes of the virtual septum of a 6.4 percent radially inwardly directed strain.
Figure 12:
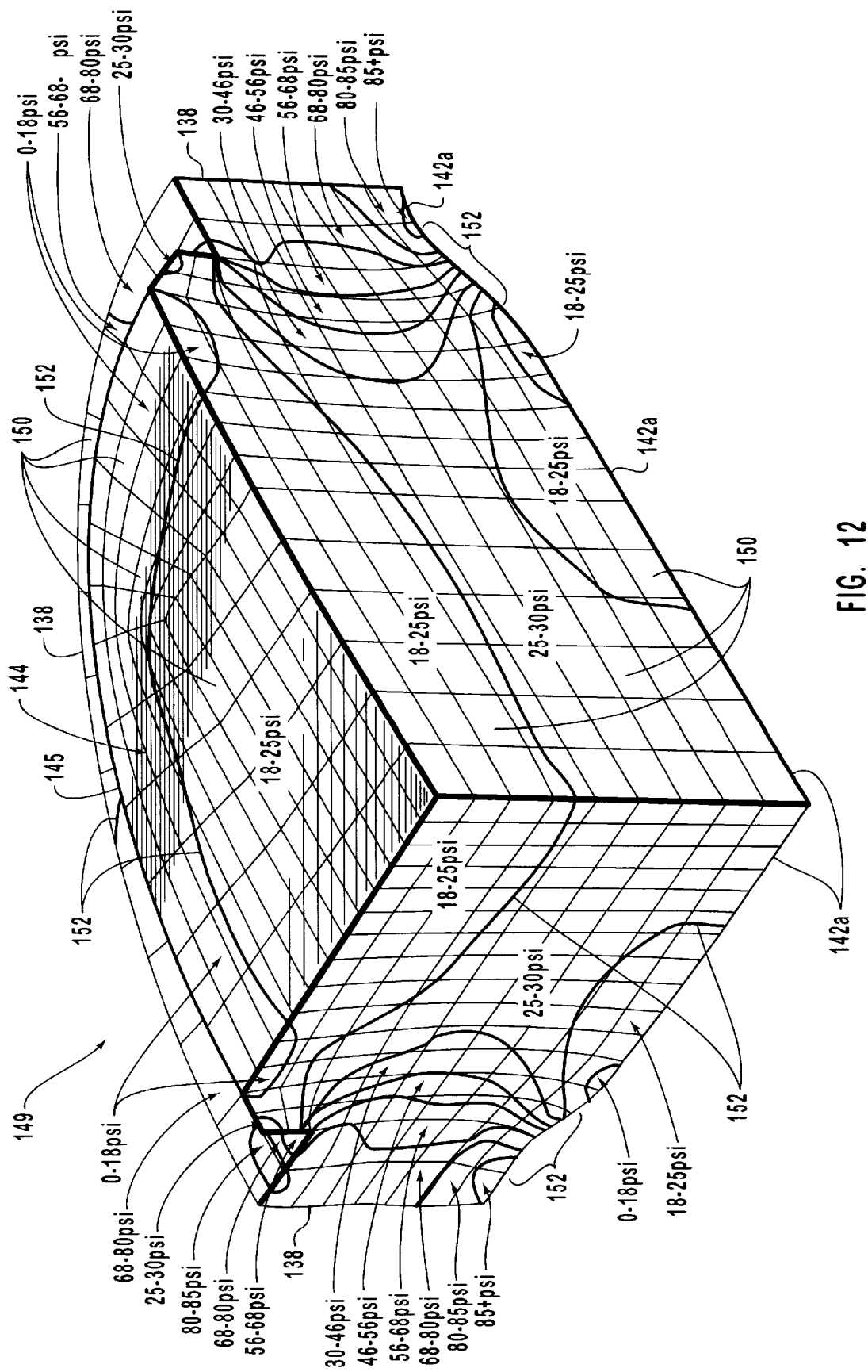
FIG. 12 is a perspective view of a diagram of the quadrant of the virtual septum and associated finite element mesh of FIG. 10 showing gradients of hydrostatic pressure produced therein by the application along the longitudinal and lateral axes of the virtual septum of a 6.4 percent radially inwardly directed strain in addition to the application to the periphery of the virtual septum of an 8.0 percent axial compression.

The analysis proceeding in a two-stage fashion is illustrated in the order of implementation first in FIG. 11 and then in FIG. 12.

First bearing surface 102 and septum support shoulder 120 were imposed against outer face 140 and inner face 142a, respectively, of virtual septum 149 about the entire periphery 138 thereof. Then, inner surface 92 was disposed in contact with periphery 138 of virtual septum 149 and moved radially inwardly, imposing forces upon periphery 138 of virtual septum 149 like those imposed on septum 91 in the installed configuration by inner surface 92 of shirt 46 of cap 42. In this manner, a radially inwardly directed strain of 6.4 percent in the plane of septum 91 was imposed on virtual septum 149 by the computer software and then presented visually.

The results are shown in FIG. 11. Hydrostatic pressure contour lines 152 depicting the hydrostatic pressure conditions in virtual septum 149 are drawn on the exterior of virtual septum 149. The ranges of hydrostatic pressure between each of hydrostatic pressure contour lines 152 are also labeled in FIG. 11. The deformation in virtual septum 149 produced by the application of the radially inwardly directed strain is most apparent in FIG. 11 along inner face 142a near periphery 138. Inner face 142a can be seen to bulge axially outwardly from the planar configuration of inner face 142a illustrated in the natural configuration of virtual septum 149 in FIG. 10. Significantly, at the degree of radially inwardly directed strain shown, hydrostatic pressure in the needle penetration region of virtual septum 149 is relatively uniform, being in a range from about 10 pounds per square inch to about 26 pounds per square inch.

Hydrostatic pressure gradient patterns of the type shown in FIG. 11 correspond to conditions of relatively uniform internal stress throughout the entire needle penetration region of an installed septum. Consequently, the needle retention force exerted upon the tip of a needle, such as needle 26 of hypodermic syringe 28, that penetrates septum 91 is substantially the same for any point in the cross section of septum 91 at which that penetration is effected. Correspondingly, the needle penetration force resisting the penetration of septum 91 by the tip of a needle, such as needle 26 of hypodermic syringe 28, is also the same for any point on the cross section of septum 91 at which that penetration is attempted to be effected. This is a most efficacious consequence, and one not previously obtainable in any systematic manner in an installed septum that was not circular.

A second aspect of the interaction of septum 91 and housing 40, however, also contributes to the development of idealized uniform stress conditions in the installed configuration of septum 91.

In yet another aspect of an access means according to teachings of the present invention clamp, means are provided for urging outer face 140 and inner face 142 of septum body 136 toward each other at periphery 138 thereof. As seen in FIG. 6, distance D between bearing surface 102 on retention lip 98 and support shoulder 120 is smaller than the peripheral thickness $T_p$ shown in FIG. 7 between inner face 142 and outer face 140 of septum body 136 at periphery 138 of septum 91. Accordingly, when septum 91 is disposed in access aperture 130 in housing 40, periphery 138 of septum 91 is axially narrowed between septum retention lip 98 and septum support shoulder 120.

Corresponding to these structural aspects of access port 18, the finite element analysis of virtual septum 149 was extended beyond that depicted in FIG. 11 to reflect the force of clamping periphery 138 of septum 91 against septum support shoulder 120 with first bearing surface 102. To do so, inner surface 92 was held fixed at a location that produced the 6.4 percent radially inwardly directed strain depicted in FIG. 11. Bearing surface 102 was held fixed, and septum support shoulder 120 was advanced axially to such an extent as to impose an 8.0 percent axial strain on virtual septum 149 about periphery 138 thereof.

The results are shown in FIG. 12. Hydrostatic pressure contour lines 152 depicting the hydrostatic pressure conditions in virtual septum 149 are drawn on the exterior of virtual septum 149. The ranges of hydrostatic pressure between each of hydrostatic pressure contour lines 152 are also labeled in FIG. 13. Accentuated deformation of virtual septum 149 relative to that observed in FIG. 11 is seen in FIG. 12 resulting from the application of the axial strain. This distortion is most apparent in FIG. 12 along inner face 142*a near periphery 138.*

Significantly, the combination of this degree of axial strain with the radially inwardly directed strain imposed on virtual septum 149 and illustrated in FIG. 12 produced relatively uniform hydrostatic pressure in the needle penetration region of virtual septum 149. The hydrostatic pressure in the needle penetration region of virtual septum 149 as illustrated in FIG. 12 is largely in a desirable range of from about 18 pounds per square inch to about 30 pounds per square inch. Also acceptable would be hydrostatic pressure in a range from about 10 pounds per square inch to a range of about 46 pounds per square inch. Ultimately, a range of from about 5 pounds per square inch to about 56 pounds per square inch is also appropriate.

These ranges of hydrostatic pressure have been determined to produce an average needle retention force equal to about 1.1±0.1 pounds. This level of needle retention force is deemed optimally desirable to clinicians and is a range in which the risks of septum coring are relatively minimal. Although somewhat less desirable, needle retention force in a range of from about 0.5 pounds to about 1.5 pounds is also acceptable. Needle retention force in a range from about 0.35 pounds to about 2.5 is somewhat less desirable, but even needle retention force in a range from about 0.2 pounds to about 3.5 pounds will suffice in many circumstances.

Figure 13:
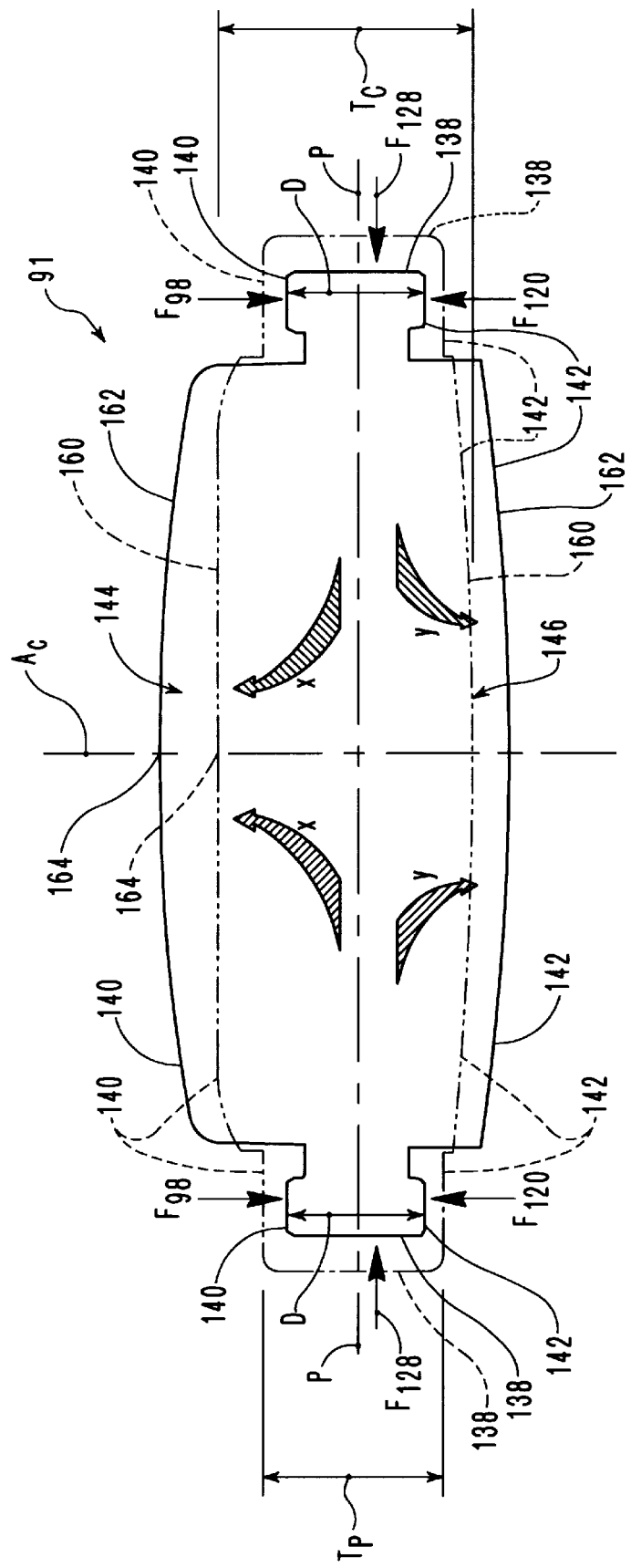
FIG. 13 is a diagram containing comparative elevation profile views superimposed on a common axis of symmetry of the septum of FIG. 3 in the natural configuration thereof shown in phantom and in the installed configuration thereof shown in solid line.

FIG. 13 portrays the effect on the profile of septum 91 of this axial deformation in combination with the radially inwardly directed movement of periphery 138 of septum 91 produced by housing 40 when septum 91 is installed in access aperture 130.

In FIG. 13, a natural configuration profile 160 of septum 91 in the natural configuration thereof is depicted in phantom. This depiction corresponds to the profile of septum 91 shown in FIG. 7. Superimposed on natural configuration profile 160 is an installed configuration profile 162 in solid line of septum 91 in the installed configuration thereof. This depiction corresponds to the profile of septum 91 shown in FIG. 8. Natural configuration profile 160 and installed configuration profile 162 are superimposed on common central axis $A_c$ of septum 91 introduced previously in FIG. 3.

Figure 8:
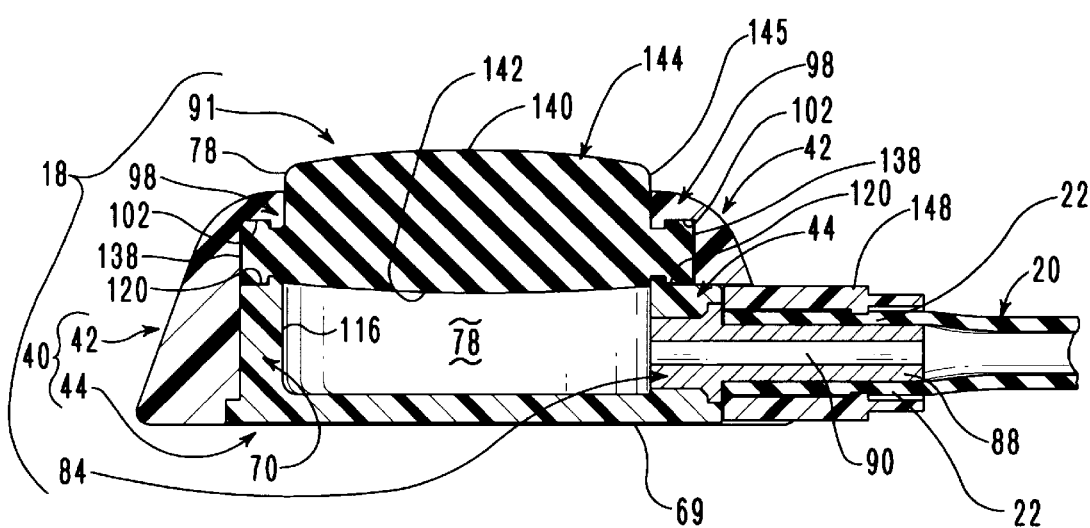
FIG. 8 is a cross-sectional elevation view of the assembled vascular access port of FIG. 2 taken along section line 8—8 shown therein.

From FIG. 8, it can be observed that periphery 138 of the installed configuration of septum 91 is enclosed on three (3) sides, respectively, by rim 128, septum retention lip 98, and septum support shoulder 120. As a result, various forces illustrated in FIG. 13 are imposed on septum 91.

A radially inwardly directed force $F_{128}$ is imposed on periphery 138 of septum 91 in plane P thereof. Force $F_{128}$ is produced by rim 128 of access aperture 130. Simultaneously, axially directed forces are imposed in opposite directions, respectively, on outer face 140 and inner face 142 of septum body 136 at periphery 138 of septum 91. A first of these axially directed forces is $F_{98}$, which is imposed on outer face 140 of septum body 136 at periphery 138 of septum 91 by septum retention lip 98. The other of the opposed axially directed forces is force $F_{120}$, which is imposed in a direction opposite to that of force $F_{98}$ on inner face 142 of septum body 136 at periphery 138 of septum 91 by septum support shoulder 120.

Accordingly, as septum 91 is urged into the installed configuration thereof, the material thereof at periphery 138 is displaced radially and axially inwardly. This inward displacement of material collectively results in turn in the axially outward displacement of needle target dome 144 indicated by arrows X. In addition, reinforcing plug 146 is displaced outwardly from septum body 136 as indicated by arrows Y.

This effect on the material of septum 91 caused by axial directed force $F_{98}$ and axially directed force $F_{120}$ enhances the sealing effectiveness of septum 91 in access aperture 130. Also enhanced is the uniformity of the hydrostatic pressure in portions of septum 91 accessible to needle penetration produced for the most part by radially inwardly directed forces $F_{128}$. The overall levels of hydrostatic pressure within the material of septum 91 should be in a broad range from about 5 pounds per square inch to about 50 pounds per square inch. More preferably, however, the hydrostatic pressure in septum 91 in the installed condition thereof should be in a range from about 10 pounds per square inch to about 40 pounds per square inch. A range from about 15 pounds per square inch to about 30 pounds per square inch is most preferred.

Clamp means according to the teachings of the present invention may optionally also include first gripping ridge 104 on cap 42 of housing 40 and second gripping ridge 122 on base 44 of housing 40. Although first gripping ridge 104 and second gripping ridge 122 axially displace toward each other outer face 140 and inner face 142 of periphery 138 of septum 91, the volume of septum material thusly urged inwardly is relatively small when compared with that resulting from force $F_{128}$ applied by rim 128 of access aperture 130, force $F_{98}$ applied by septum retention lip 98, and force $F_{120}$ applied by septum support shoulder 120. First gripping ridge 104 and second gripping ridge 122, therefor function primarily to retain periphery 138 of septum 91 securely in access aperture 130 in the installed configuration thereof. Doing so markedly prevents buckling or movement of septum 91 in access aperture 130 in reaction to the forces depicted in FIG. 13.

The design of an acceptable elongated vascular access port, such as vascular access port 18, affords for wide variation in and among the parameters of the septum utilized therewith. These septum parameters can be altered substantially at will toward the goal of producing in a single elongated access port one or more optimum characteristics in the installed configuration of the septum.

For example, as the central thickness $T_c$ of septum 91 increases, characteristics like needle sealing, needle penetration, and needle retention in septum 91 correspondingly increase. On the other hand, it may be desirable to minimize the size or thickness of septum 91 in order to reduce the overall size of the vascular access port in which septum 91 is to be installed. Thus, compromise is required among the goals of optimum septum characteristics in the installed septum and the size of a vascular access port, even if constructed according to the teachings of the present invention. Such tradeoffs are common in designing a vascular access port suitable for a specific specialized use.

Another example may provide further illumination. If central thickness $T_c$ of septum 91 decreases, and if it is desired nonetheless to maintain some predetermined level of septum characteristics in the installed septum, then radially inwardly directed force $F_{128}$ imposed on periphery 138 of septum 91 in the installed configuration by rim 128 can be increased. If septum 91 is extremely thin, however, the radially inwardly directed force $F_{128}$ needed to maintain predetermined septum characteristics may be so great as to preclude the positioning of septum 91 in access aperture 130 manually during the assembly of vascular access port 18. The additional manufacturing cost of doing so by machine may outweigh the advantage of a very thin septum in the application envisioned.

Furthermore, as central thickness $T_c$ of septum 91 is decreased and compensatingly radially inwardly directed force $F_{128}$ imposed at periphery 138 thereof is increased, the chance of buckling, pinching, or dimpling in the installed configuration of septum 91 is increased. These consequences represent undesirable examples of the loss of structural stability in the installed configuration of septum 91. Any loss of structural stability in the installed configuration of septum 91 endangers the maintenance of desirable septum characteristics. Thus, buckling, pinching, or dimpling in an installed septum are always objectionable, regardless of the nature of the septum characteristics attained. If structural stability does not exist in an installed septum, desirable septum characteristics may correspondingly not be stably maintained.

Accordingly, in yet another aspect of the present invention, a septum, such as septum 91, is provided with support means for preventing buckling in the installed configuration of the septum. By way of example and not limitation, needle target dome 144 is integrally formed with septum 91 on outer face 140 of septum body 136. Alternatively, or in addition thereto, reinforcing plug 146 is integrally formed with septum 91 on inner face 142 thereof. Each of needle target dome 144 and reinforcing plug 146, respectively, increases the thickness of septum body 136 in the vicinity of center 164 of septum 91. This in turn prevents buckling or dimpling in septum 91, but does so without increasing the peripheral thickness $T_p$ of septum 91. This arrangement permits the effective thickness of septum 91 to be enhanced without correspondingly increasing the size of vascular access port 18.

The thickness and configuration of needle target dome 144 and reinforcing dome 146 may be varied for different specific applications. The design of these structures interacts closely in arriving at any desired objective with the overall size of septum 91 in the plane P thereof and the amount of radially inwardly directed force $F_{128}$ intended to be applied in installing septum 91.

An additional parameter that can be adjusted to vary the degree of hydrostatic pressure in the installed configuration of septum 91 is the degree of the mutually oppositely directed axial displacement effected in outer face 140 and inner face 142 at periphery 138 of septum body 136. By increasing the axial displacements at periphery 138 of septum body 136, the central thickness $T_c$ of septum 91 or the radially inwardly directed force $F_{128}$ imposed on septum 91 may to an extent be compensatingly decreased.

The present invention envisions that vascular access ports can be designed in which the characteristics of the septum installed therein are achieved at will by varying independently or in combination the thickness of the septum, the degree of radially inwardly directed forces imposed on the septum, or the extent of the axial compression of the periphery of the septum effected to achieve installation. It is contemplated, for example, that resort may be made toward such ends to the use of a septum retention lip 98 and septum support shoulder 120 having a nonuniform distance D therebetween. This can be attained by altering the separation between septum retention lip 98 and septum support shoulder 120 in selected regions about access aperture 130.

Desirable patterns of uniform hydrostatic pressure in the installed configuration of a septum can be produced in a variety of configurations of elongated septums.

Figure 14:
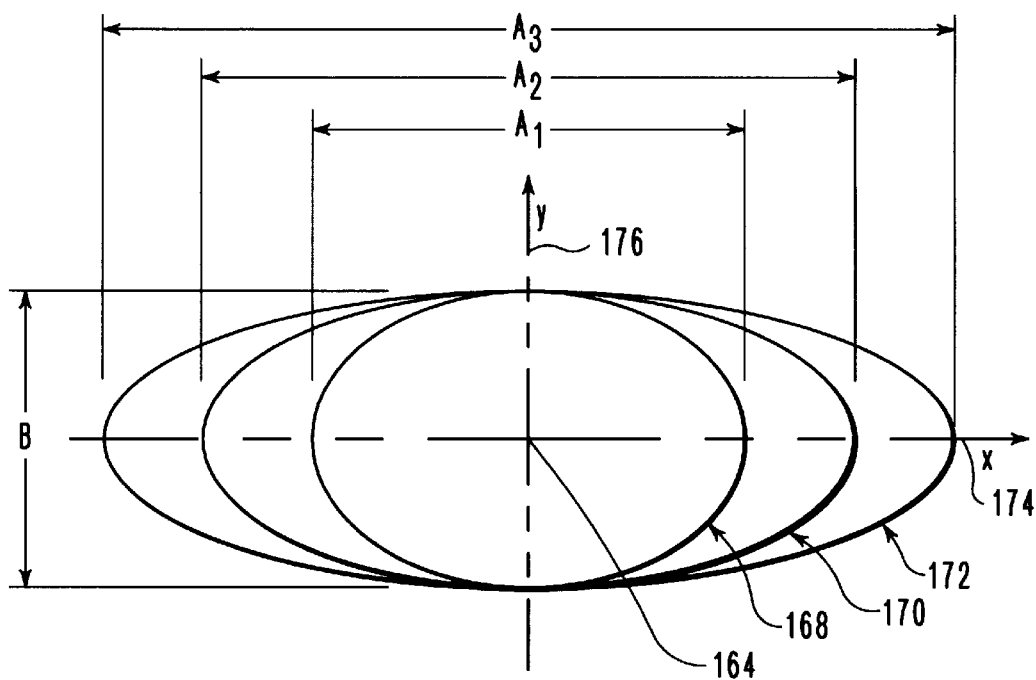
FIG. 14 is a comparative plan view of a first family of elliptical septums of identical length that incorporate teachings of the present invention and exhibit differing configurations.

For example, depicted in FIG. 14 in plan view is a first family of elliptical septums 168, 170, and 172 which has been superimposed on a single coordinate axis. Like the coordinate axis illustrated in FIG. 9, that in FIG. 14 includes an X-axis that is coincident with the common longitudinal axis 174 of the first family of septums and a Y-axis that is coincident with the common lateral axis 176 of the first family of septums. The origin of the coordinate axis is positioned at common center 164 of the first family of septums.

Septums 168, 170, and 172 share a common width B measured along lateral axis 176, but vary among each other in length as measured along common longitudinal axis 174 thereof. Septum 172 with the greatest length $A_3$ has an aspect ratio and an eccentricity that are greater than those of either of septum 168 or septum 170. Correspondingly, septum 168 with the smallest length $A_1$ has an aspect ratio and an eccentricity that are less than those of either septum 170 or septum 172.

Nonetheless, in each case, utilizing the principles disclosed above, it is possible to design an appropriate corresponding housing and access aperture in which to install any of first family of septums 168, 170, or 172, while producing uniform hydrostatic pressure characteristics in the installed configuration of each.

Figure 15:
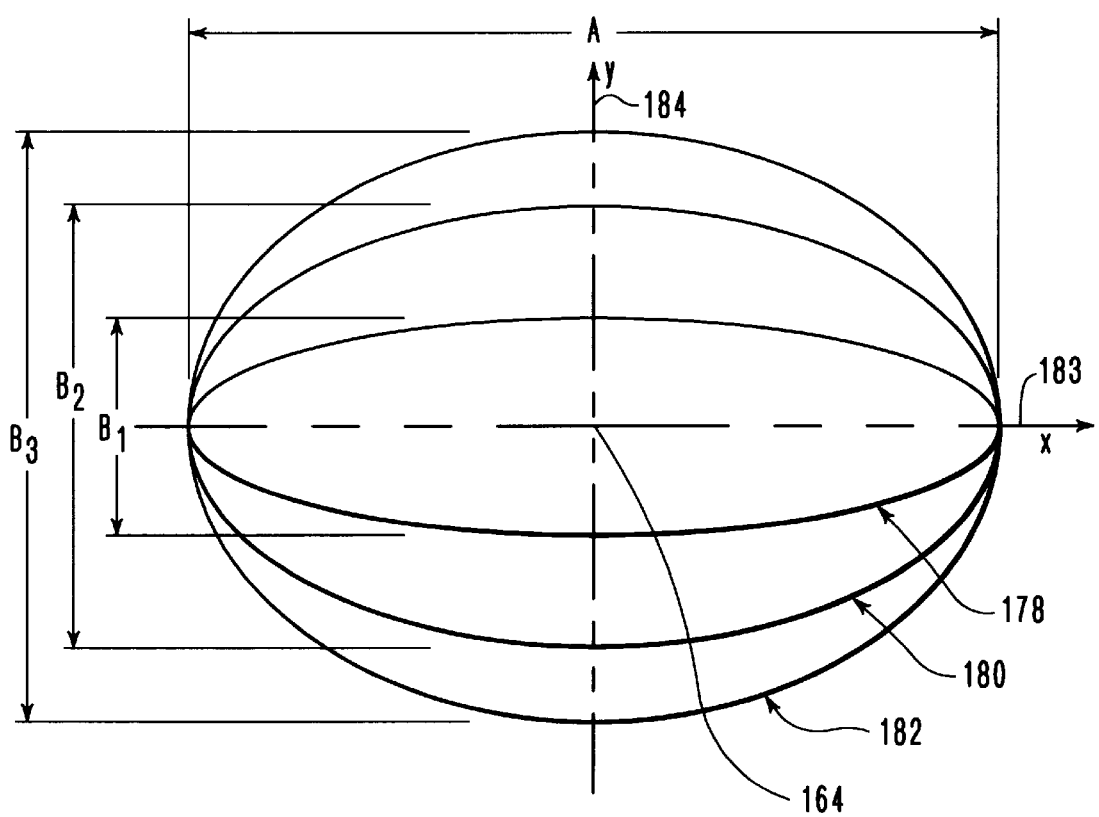
FIG. 15 is a comparative plan view of a second family of elliptical septums of identical width that incorporate teachings of the present invention and exhibit differing configurations.

A second family of elliptical septums 178, 180 and 182 is depicted in FIG. 15. There, as in FIG. 14, the second family of septums has been superimposed on a coordinate axis having the origin thereof positioned at common center 164 of the second family of septums. The coordinate axis of FIG. 15 includes an X-axis that is coincident with the common longitudinal axis 183 of the second family of septums and a Y-axis that is coincident with the common lateral axis 184 of the second family of septums.

Septums 178, 180 and 182 share a common maximum extent, or length A, measured along common longitudinal axis 183, but the width of each respective septum measured along lateral axis 184 varies throughout the second family of septums. As septum 182 has the largest width $B_3$, septum 182 has an aspect ratio and an eccentricity that are smaller than those associated with either septum 180 or septum 178. Correspondingly, as septum 178 has the smallest width $B_1$, septum 178 has an aspect ratio and an eccentricity that are larger than those associated with either septum 180 or septum 182.

Nonetheless, in each case, utilizing the principles disclosed above, it is possible to design an appropriate corresponding housing and access aperture in which to install any of second family of septums 178, 180, and 182, while producing uniform stress characteristics in the installed configuration of each.

Septums 172, 170 and 168 in FIG. 14 and septums 178, 180 and 182 in FIG. 15 are examples of a very particular category of the elongated septums that incorporate teachings of the present invention. The septums illustrated in FIGS. 14 and 15 are referred to as "truly elliptical." A truly elliptical septum has an outer periphery that is defined by the following single continuous mathematical relationship:

$$\frac{x^2}{a^2} + \frac{y^2}{b^2} = 1, \quad \text{where:} \quad [6]$$

2a=the length of ellipse along the longitudinal axes thereof;

2b=the width of the ellipse taken perpendicular to the length; and

P(x, y) is any point on the outer periphery of the truly elliptical septum.

The eccentricity E of a septum that is truly elliptical is as a result determined by the following equation, which is reminiscent of Equation No. 1:

$$E = \sqrt{1 - \left(\frac{b}{a}\right)^2} \quad [7]$$

Elongated septums within the scope of the present invention include many types of septums other than just septums that are truly elliptical.

Figure 16:
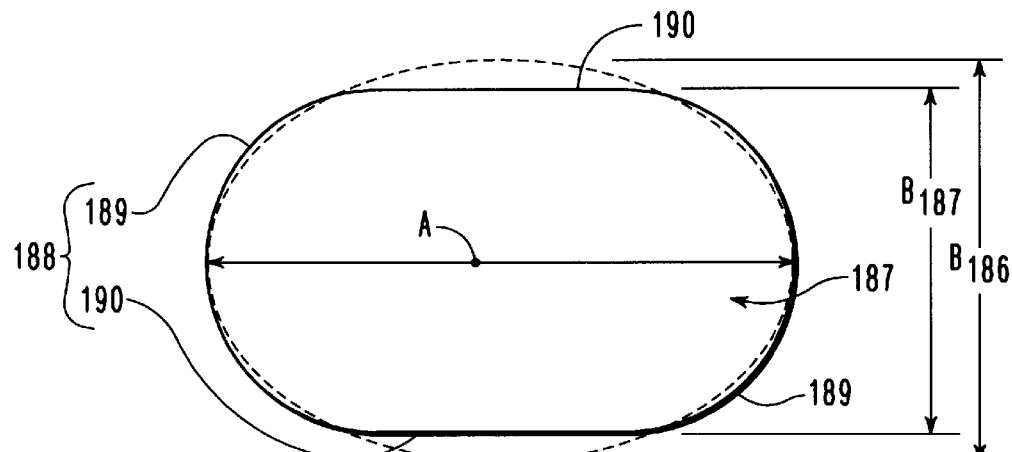
FIG. 16 is a comparative plan view of a truly elliptical septum in dashed line superimposed on the plan view of an oval septum that incorporates teachings and obtains benefits of the present invention.

For example, depicted in FIG. 16 in dashed line is a truly elliptical septum 186 upon which has been superimposed an oval septum 187 having a periphery 188 that is at several locations almost congruent with the periphery of truly elliptical septum 186. Periphery 188 of oval septum 187, however, comprises respective semicircular extreme ends 189 tangentially interconnected by a pair of straight sides 190. While oval septum 187 and truly elliptical septum 186 have equal lengths A, the width $B_{187}$ of oval septum 187 is less than the width $B_{186}$ of truly elliptical septum 186. This results in a higher aspect ratio and eccentricity in truly elliptical septum 186 than in oval septum 187.

It should be noted, however, that by appropriately increasing the radius of curvature of semicircular ends 189 of an oval septum, such as septum 187, it is possible to produce an alternative oval septum having a length A and a width equal to width $B_{186}$ of truly elliptical septum 186. This would result in equal aspect ratios and eccentricities in truly elliptical 186 and the alternative oval septum, but the alternative oval septum would have a larger target area than would truly elliptical septum 186.

These comparative features of each of the septums depicted in FIG. 16 might advantageously be utilized in the design of an elongated vascular access port for a specific intended use. Nonetheless, both of the septums illustrated in FIG. 16 are elongated within the scope of the present invention, and oval septum 187, while not being truly elliptical, is in several design respects substantially elliptical.

Figure 17:
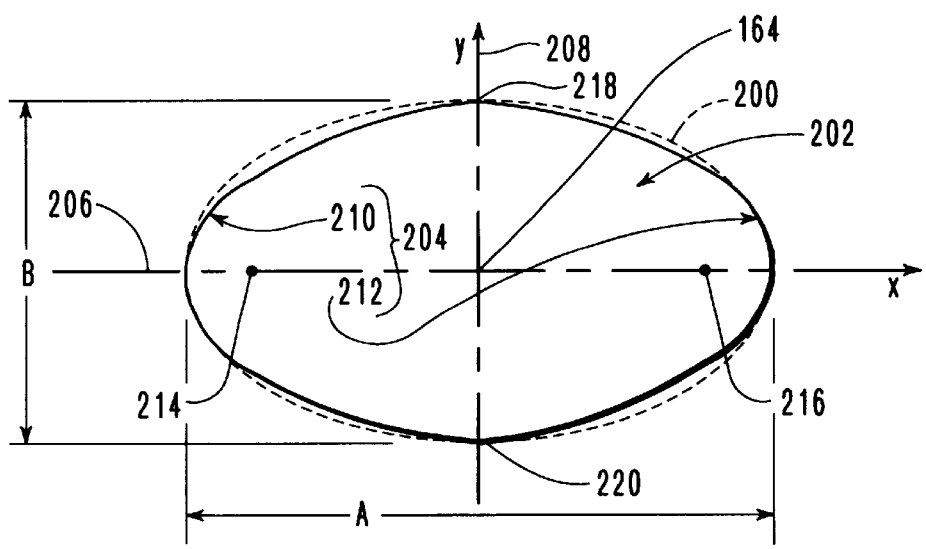
FIG. 17 is a comparative plan view of a truly elliptical septum in dashed line superimposed on the plan view of a septum in solid line having parabolic extremes that incorporates teachings and obtains benefits of the present invention.

In a similar manner, illustrated in FIG. 17 in dashed line is a truly elliptical septum 200 superimposed upon an elongated septum 202 having, mathematically, a relatively complex periphery 204. For convenience of analysis, both truly elliptical septum 200 and elongated septum 202 have in turn been superimposed upon a coordinate axis having the origin thereof located at common center 164 of the septums depicted. The coordinate axis of FIG. 17 includes an X-axis that coincides with the longitudinal axis 206 of both true elliptical septum 200 and elongated septum 202 and a Y-axis that coincides with the common lateral axis 208 of each.

Longitudinal axis 206 intersects periphery 204 of elongated septum 202 at a first extreme end portion 210 and an opposed second extreme end portion 212. First extreme end portion 210 and second extreme end portion 212 are each symmetrical about common longitudinal axis 206. In the embodiment illustrated, first extreme end portion 210 and second extreme end portion 212 are also mirror images of each other. First extreme end portion 210 intersects second extreme end portion 212 nontangentially at a first vertex 218 and a second vertex 220, each of which is disposed on common lateral axis 208.

The periphery of first extreme end portion 210 and of second extreme end portion 212 are each substantially parabolic. Accordingly, the point at which the periphery of first extreme end portion 210 intersects longitudinal axis 206 is referred to as the vertex of first extreme end portion 210. Similarly, the point at which second extreme end portion 212 intersects longitudinal axis 206 is referred to as the vertex of second extreme end portion 212. Also, the periphery of first extreme end portion 210 and the periphery of second extreme end portion 212 each have a corresponding associated focal point that is disposed interior of periphery 204 of elongated septum 202. These are focal point 214 corresponding to first extreme end portion 210 and focal point 216 corresponding to second extreme end portion 212.

A parabolic end portion of a septum has an outer periphery that is defined by the following mathematical relationship:

$$Y^2 = 2ax, \quad [8]$$

where:
   a=the distance between the vertex and the focal point of the parabolic curve.

In view of the distinctive mathematical shape of extreme end portion 210 and extreme end portion 212, septum 202 will be referred to hereinafter as "parabolic-ended" septum 202. It should be noted that parabolic-ended septum 202 and truly elliptical septum 200 each have identical lengths A and widths B. Therefore, the aspect ratio and eccentricity of each are equal, respectively.

It has been determined by experimentation that the ability to produce uniform hydrostatic pressure characteristics in a septum, such as parabolic-ended septum 202, is enhanced relative to the ability to do so in connection with other types of elongated septums, even truly elliptical septums, such as truly elliptical septum 200. Nonetheless, parabolic-ended septum 202 has a slightly smaller surface area than that of truly elliptical septum 200 and would accordingly present a smaller needle target area than would truly elliptical septum 200, despite the identical length A and width B of each.

These comparative features of each of the septums depicted in FIG. 17 might advantageously be utilized in the design of an elongated vascular access port for a specific intended use. Nonetheless, both of these septums illustrated in FIG. 17 are elongated within the scope of the present invention, and parabolic-ended septum 202, while not being truly elliptical, is in several design respects substantially elliptical.

Figure 18:
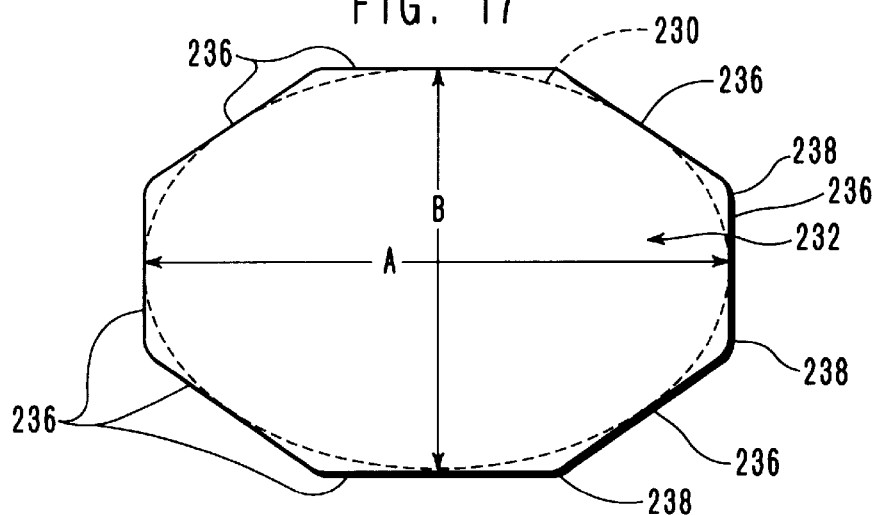
FIG. 18 is a comparative plan view of a truly elliptical septum in dashed lines superimposed on the plan view of a septum in solid line having a polygonal periphery that incorporates teachings and obtains benefits of the present invention.

FIG. 18 presents yet another such comparison. There a truly elliptical septum 230 is shown in dashed line superimposed upon an elongated septum 232 with a periphery that includes a plurality of straight sides 236 that intersect each other at vertices 238. Straight sides 236 need not be equal in length or in any way symmetrically disposed, although the latter characteristic is apparent in elongated septum 232. Neither need straight sides 236 be tangential to any truly elliptical septum, such as truly elliptical septum 230, as is the case for straight sides 236 shown in FIG. 18. Alternative polygonal configurations utilizing fewer or more straight sides than the eight (8) such sides illustrated in FIG. 18 would also be appropriate.

In view of the shape of the periphery of elongated septum 232, elongated septum 232 will be referred to hereinafter as "polygonal" septum 232. It should be noted that truly elliptical septum 230 and polygonal septum 232 each have identical length A and width B. Therefore, the aspect ratio and the eccentricity of each are equal, respectively. Polygonal septum 232 has a slightly larger surface area than that of truly elliptical septum 230 and accordingly might be expected to present a larger needle target area than would truly elliptical septum 230, despite the identical length A and width B of each.

These comparative features of each of the septums depicted in FIG. 18 might advantageously be utilized in the design of an elongated vascular access port for a specific intended use. Nonetheless, both of the septums illustrated in FIG. 18 are elongated within the scope of the present invention, and polygonal septum 232, while not being truly elliptical, is in several design respects substantially elliptical.

Polygonal septum 232 is presented in order to demonstrate that the teachings of the present invention contemplate the use of elongated septums in a diverse range of shapes. These shapes may be considered substantially elliptical, but if not so considered, septums of such shapes can yet be installed in the housing of a vascular access port, if the access aperture in the housing thereof is designed according to the above teachings of the present invention for producing uniform stress characteristics in the installed configuration of the septum. By so doing, numerous vascular access ports can be provided, that are elongated and streamlined in shape, and therefore susceptible to successful implantation in small tissue areas, such as in the extremities of an adult patient or in the body of an infant or a small child. Such elongated vascular access ports need not, however, suffer any reduction in needle target area in the septum utilized therewith or exhibit undesirable irregularities in needle sealing, needle retention, or needle penetration characteristics. Septums with needle target domes with eccentricities of 0.81, 0.90, or higher can be incorporated into access devices. The insights and discoveries disclosed above free the design of future vascular access ports from the limitations and disadvantages brought about by an exclusive reliance upon septums that are round in cross section.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable vascular access port comprising:
   (a) a needle-impenetrable housing enclosing a fluid reservoir, said housing having formed therethrough an access aperture communicating between said fluid reservoir and the exterior of said housing, said access aperture having a generally elongated rim and extreme ends defining therebetween the maximum extent of said access aperture;
   (b) an outlet stem projecting from said housing at a location adjacent one of said extreme ends of said access aperture. said outlet stem enclosing a longitudinal fluid passageway extending from the end of said outlet stem remote from said housing through said housing to said fluid reservoir; and
   (c) an elastomeric, needle-penetrable, generally planar septum, said septum having a periphery in a cross section of said septum taken in the plane thereof that is geometrically proportional to and larger than said rim of said access aperture, said septum being disposed in said access aperture with said periphery of said septum in sealing engagement with said rim of said access aperture, whereby in disposing said septum in said access aperture said periphery of said septum is displaced inwardly in a direction parallel to said plane of said septum by said rim of said access aperture.

2. An access port as recited in claim 1, wherein said housing comprises:
   (a) a base comprising a floor and a continuous encircling sidewall upstanding therefrom, the interior of said base corresponding to said fluid reservoir of said housing; and
   (b) a cap comprising a top wall and a skirt depending therefrom, said cap being configured to receive in said skirt thereof the end of said sidewall of said base remote from said floor thereof, and said access aperture being formed through said top wall of said cap at a location that communicates with said fluid reservoir of said housing when said sidewall of said base is received in said skirt of said cap.

3. An access port as recited in claim 2, wherein:
(a) said sidewall of said base terminates remote from said floor of said base in a continuous septum support shoulder disposed in a plane parallel to said floor of said base; and
(b) said cap comprises a septum retention lip projecting radially inwardly into said access aperture from the side of said rim thereof adjacent the exterior of said top wall of said cap, said septum retention lip having a generally planar bearing surface on the side of said septum retention lip opposite from the exterior of said top wall of said cap, said bearing surface of said septum retention lip being in parallel spaced-apart relationship to said septum support shoulder, when said sidewall of said base is received in said skirt of said cap.

4. An access port as recited in claim 3, wherein the edge of said septum retention lip remote from said rim of said access aperture is geometrically proportional to and smaller than said shape of said rim of said access aperture.

5. An access port as recited in claim 4, wherein said edge of said septum retention lip is congruent with the cross section of said fluid reservoir taken in a plane parallel to said floor of said base of said housing.

6. An access aperture as recited in claim 3, further comprising:
(a) a first septum gripping ridge projecting from and normal to said bearing surface of said septum retention lip; and
(b) a second septum gripping ridge projecting from and normal to said septum support shoulder.

7. An access port as recited in claim 6, wherein:
(a) said first septum gripping ridge is disposed along the edge of said bearing surface of said septum retention lip adjacent said fluid reservoir; and
(b) said second septum gripping ridge is disposed along the edge of said septum support shoulder remote from said rim of said access aperture.

8. An access port as recited in claim 3, wherein said periphery of said septum is thicker than the distance between said septum support shoulder and said bearing surface of said septum retention lip, when said sidewall of said base is received in said skirt of said cap, whereby said periphery of said septum is axially compressed between said septum support shoulder and said bearing surface of said septum retention lip when said sidewall of said base is received in said skirt of said cap with said septum disposed in said access aperture.

9. An access port as recited in claim 2, wherein said access aperture has a longitudinal axis coincident with the maximum extent of said access aperture, and said longitudinal axis of said access aperture intersects said rim thereof at respective extreme ends of said access aperture, and said outlet stem projects from said housing at a location adjacent one of said extreme ends of said access aperture.

10. An access port as recited in claim 9, wherein said outlet stem is carried by said base of said housing and projects through said skirt of said cap of said housing when said sidewall of said base is received in said skirt of said cap.

11. An access port as recited in claim 2, wherein said skirt of said cap is a single continuous structure encircling said sidewall of said base when said sidewall of said base is received in said skirt of said cap.

12. An access port as recited in claim 1, wherein said access aperture has a longitudinal axis coincident with the maximum extent of said access aperture, and said longitudinal axis of said access aperture intersects said rim thereof at respective extreme ends of said access aperture, and said outlet stem projects from said housing at a location adjacent one of said extreme ends of said access aperture.

13. An implantable vascular access port comprising:
(a) a needle-impenetrable housing enclosing a fluid reservoir, said housing having formed therethrough an access aperture communicating between said fluid reservoir and the exterior of said housing, said access aperture being defined by a continuous elongated encircling rim, and said housing further including a septum support shoulder projecting radially inwardly into said access aperture at the side of said rim of said access aperture opposite from said exterior of said housing, the edge of said septum support shoulder remote from said rim of said access aperture defining said fluid reservoir, whereby said fluid reservoir at said septum support shoulder is smaller than said access aperture at said support shoulder; and
(b) an elastomeric, needle-penetrable, generally planar septum, said septum being disposed in and sealing said access aperture in an installed configuration of said septum with the periphery of said septum in continuous engagement with said rim of said access aperture, said septum in said installed configuration thereof being precluded from entering said fluid reservoir bv said septum support shoulder said septum when free of externally imposed forces being capable of assuming a natural configuration wherein the periphery of the cross section of said septum taken in the plane thereof is geometrically proportional to and larger than said rim of the access aperture, whereby in assuming said installed configuration said periphery of said septum is displaced inwardly in said plane of said septum relative to said natural configuration thereof by forces imposed on said periphery of said septum by said rim of said access aperture.

14. An access port as recited in claim 13, wherein said septum comprises:
(a) an outer face on the side of said septum oriented to the exterior of said housing in said installed configuration of said septum;
(b) an inner face on the side of said septum opposite from said outer face; and
(c) support means integrally formed with said septum for preventing buckling of said septum in said installed configuration thereof.

15. An access port as recited in claim 14, wherein said support means comprises a needle target dome on said outer face of said septum.

16. An access port as recited in claim 15, wherein said needle target dome is smaller in extent than said outer face of said septum.

17. An access port as recited in claim 15, wherein in said installed configuration of said septum said needle target dome is displaced toward the exterior of said housing by said forces imposed on said periphery of said septum by said rim of said access aperture.

18. An access port as recited in claim 14, wherein said support means comprises a reinforcing plug on said inner face of said septum.

19. An access port as recited in claim 18, wherein said reinforcing plug is smaller in extent than said inner face of said septum.

20. An access port as recited in claim 18, wherein in said installed configuration of said septum said reinforcing plug is displaced toward the interior of said housing by said forces imposed on said periphery of said septum by said rim of said access aperture.

21. An access port as recited in claim 13, wherein said forces imposed on said periphery of said septum by said rim of said access aperture in said installed configuration of said septum produce substantially uniform hydrostatic pressure in the portion of said septum accessible for needle penetration in said installed configuration of said septum.

22. An access port as recited in claim 21, wherein said substantially uniform hydrostatic pressure in said portion of said septum is in a range from about 5 pounds per square inch to about 56 pounds per square inch.

23. An access port as recited in claim 21, wherein said substantially uniform hydrostatic pressure in said portion of said septum is in a range from about 10 pounds per square inch to about 46 pounds per square inch.

24. An access port as recited in claim 21, wherein said substantially uniform hydrostatic pressure in said portion of said septum is in a range from about 18 pounds per square inch to about 30 pounds per square inch.

25. An access port as recited in claim 13, wherein said periphery of said septum in said cross section thereof is substantially elliptical.

26. An access port as recited in claim 13, wherein:
   (a) said septum has a longitudinal axis coincident with the maximum extent of said septum in said plane thereof, said longitudinal axis of said septum intersecting said periphery of said septum at respective longitudinal extremes of said septum, said longitudinal extremes of said septum being inwardly displaced from said natural configuration thereof into said installed configuration thereof by substantially equal nonzero first displacements directed parallel to said longitudinal axis of said septum;
   (b) said septum has a lateral axis coincident with the maximum extent of said septum in said plane thereof measured perpendicular to said longitudinal axis of said septum, said lateral axis of said septum intersecting said periphery of said septum at respective medial extremes of said septum, said medial extremes of said septum being inwardly displaced from said natural configuration thereof into said installed configuration thereof by substantially equal nonzero second displacements directed parallel to said lateral axis of said septum; and
   (c) the ratio of the combination of said first displacements to said distance between said longitudinal extremes of said septum in said natural configuration thereof is equal to the ratio of the combination of said second displacements to said distance between said medial extremes of said septum in said natural configuration thereof.

27. An access port as recited in claim 13, wherein:
   (a) said septum has a longitudinal axis coincident with the maximum extent of said septum and a lateral axis coincident with the minimum extent of said septum measured perpendicular to said longitudinal axis of said septum, said longitudinal axis of said septum and said lateral axis of said septum defining a plane of said septum;
   (b) the distance between a first pair of points on said periphery of said septum disposed on said longitudinal axis thereof is reduced in said installed configuration relative to said natural configuration by a first compression distance;
   (c) the distance between a second pair of points on said periphery of said septum disposed on said lateral axis is reduced in said installed configuration relative to said natural configuration by a second compression distance; and
   (d) the ratio of said first compression distance to said distance between said first pair of points in said natural configuration of said septum is equal to the ratio of said second compression distance to said distance between said second pair of points in said natural configuration of said septum.

28. An implantable vascular access port comprising: (a) an elastomeric, needle-penetrable, generally planar septum having an elongated periphery in a cross section of said septum taken in the plane thereof; and
   (b) a needle-impenetrable housing defining:
      (i) a fluid reservoir enclosed within said housing;
      (ii) a target aperture formed in the exterior of said housing;
      (iii) a septum receiving aperture communicating between said target aperture and said fluid reservoir, said septum receiving aperture having a generally elongated rim and extreme ends defining therebetween the maximum extent of said septum receiving aperture, said rim of said septum receiving aperture being geometrically proportional to and smaller than said periphery of said septum, said septum being disposed in said septum receiving aperture with said rim of said septum receiving aperture inwardly displacing said periphery of said septum; and
      (iv) a longitudinal fluid passageway communicating between said fluid reservoir and said exterior of said housing through an outlet stem projecting from said housing at a location adjacent one of said extreme ends of said septum receiving aperture.

29. An access port as recited in claim 28, wherein said housing comprises a septum retention lip projecting radially inwardly into said septum receiving aperture from said rim of said septum receiving aperture at the side thereof adjacent said exterior surface of said housing, the edge of said septum retention lip remote from said rim of said septum receiving aperture defining the periphery of said target aperture.

30. An access port as recited in claim 29, wherein said housing comprises a septum support shoulder projecting radially inwardly from said rim of said septum receiving aperture at the side thereof opposite said septum retention lip, the edge of said septum support shoulder remote from said rim of said septum receiving aperture being coincident with the periphery of said fluid reservoir.

31. An access port as recited in claim 30, wherein said edge of said septum support shoulder remote from said rim of said septum receiving aperture is substantially elliptical.

32. An access port as recited in claim 30, wherein said periphery of said septum is compressed between said septum retention lip and said septum support shoulder when said septum is disposed in said septum receiving aperture.

33. An access port as recited in claim 29, wherein said edge of said septum retention lip remote from said rim of said septum receiving aperture is substantially elliptical.

34. An access port as recited in claim 28, wherein the cross section of said septum taken in said plane thereof is substantially elliptical.

35. An access port as recited in claim 28, wherein said target aperture is substantially elliptical in the plane thereof.

36. An access port as recited in claim 28, wherein said septum is comprised of a material having a Shore "A" durometer in a range from about 25 to about 85.

37. An access port as recited in claim 28, wherein said septum is comprised of a material having a Shore "A" durometer in a range from about 35 to about 75.

38. An access port as recited in claim 28, wherein said septum is comprised of a material having a Shore "A" durometer in a range from about 45 to about 65.

39. An access port as recited in claim 28, wherein said septum comprises.
  (a) an outer face on the side of said septum oriented to said exterior surface of said housing in an installed configuration of said septum;
  (b) an inner face on the side of said septum opposite from said outer face; and
  (c) support means integrally formed with said septum for preventing buckling of said septum in said installed configuration thereof.

40. An implantable vascular access port comprising:
  (a) a needle-impenetrable housing enclosing a fluid reservoir, said housing comprising:
    (i) a base comprising a floor and a continuous encircling sidewall upstanding therefrom, said sidewall terminating in a continuous septum support shoulder remote from said floor, the space interior of said sidewall of said base corresponding to said fluid reservoir of said housing; and
    (ii) a cap configured to receive said septum support shoulder and said sidewall of said base, said cap having formed therethrough an access aperture that communicates with said fluid reservoir of said housing when said septum support shoulder and said sidewall of said base are received in said cap, said access aperture having an elongated rim comprising a continuous encircling surface oriented perpendicular to the plane of said access aperture;
  (b) an elastomeric, needle-penetrable, generally planar septum, said septum being disposed in and sealing said access aperture in an installed configuration of said septum with the periphery of said septum in continuous engagement with said rim of said access aperture and with the periphery of said septum secured against said septum support shoulder of said sidewall of said base by said cap, said septum when free of externally imposed forces being capable of assuming a natural configuration wherein said periphery of said septum in a cross section taken in the plane thereof is geometrically proportional to and larger than the rim of said access aperture, whereby in assuming said installed configuration said periphery of said septum is displaced inwardly in said plane of said septum relative to said natural configuration thereof by forces imposed on said periphery of said septum by said rim of said access aperture; and
  (c) an outlet stem projecting from said housing and enclosing a longitudinal fluid passageway communicating between the end of said outlet stem remote from said housing through said housing to said fluid reservoir.

41. An access port as recited in claim 40, wherein:
  (a) said septum has a longitudinal axis coincident with the maximum extent of said septum in said plane thereof, said longitudinal axis of said septum intersecting said periphery of said septum at respective longitudinal extremes of said septum, said longitudinal extremes of said septum being inwardly displaced from said natural configuration thereof into said installed configuration thereof by substantially equal nonzero first displacements directed parallel to said longitudinal axis of said septum;
  (b) said septum has a lateral axis coincident with the maximum extent of said septum in said plane thereof measured perpendicular to said longitudinal axis of said septum, said lateral axis of said septum intersecting said periphery of said septum at respective medial extremes of said septum, said medial extremes of said septum being inwardly displaced from said natural configuration thereof into said installed configuration thereof by substantially equal nonzero second displacements directed parallel to said lateral axis of said septum; and
  (c) the ratio of the combination of said first displacements to the distance between said longitudinal extremes of said septum in said natural configuration thereof is equal to the ratio of the combination of said second displacements to the distance between said medial extremes of said septum in said natural configuration thereof.

42. An access port as recited in claim 40, wherein the cross section of said septum taken in said plane thereof is substantially elliptical.

43. An access port as recited in claim 40, wherein said septum comprises:
  (a) a substantially planar septum body having an outer face on a side of said septum oriented to the exterior of said housing in said installed configuration of said septum and an inner face on the side of said septum opposite from said outer face;
  (b) a needle target dome on said outer face of said septum body; and
  (c) a reinforcing dome on said inner face of said septum body.

44. An access port as recited in claim 40, wherein said base and said cap are comprised of plastic.

45. An access port as recited in claim 40, wherein said base and said cap are comprised of metal.

46. An access port as recited in claim 40, wherein said septum is comprised of silicone.

47. An implantable vascular access port comprising:
  (a) a needle-impenetrable housing enclosing a fluid reservoir, said housing comprising:
    (i) a top wall having formed therethrough an elongated access aperture communicating between said fluid reservoir and the exterior of said housing; and
    (ii) a septum support shoulder projecting radially inwardly into said access aperture at the side thereof opposite from said exterior of said housing, the edge of said septum support shoulder remote form said access aperture defining said fluid reservoir whereby said fluid reservoir at said septum support shoulder is smaller than said access aperture at said support shoulder; and
  (b) an elastomeric, needle-penetrable, generally planar, elongated septum having a periphery in a cross section of said septum taken in the plan thereof that encloses an area larger than the cross-sectional area of said access aperture, said septum being disposed in said access aperture in an installed configuration thereof wherein forces exerted on said septum by said access aperture inwardly displace said periphery of said septum and produce substantially uniform hydrostatic pressure in the portion of said septum accessible for needle penetration in said installed configuration of said septum, said septum in said installed configuration being precluded from entering said fluid reservoir by said septum support shoulder.

48. An access port as recited in claim 47, wherein said septum comprises:

(a) an outer face on the side of said septum oriented to the exterior of said housing when said septum is disposed in said access aperture;

(b) an inner face on the side of said septum opposite from said outer face; and (c) a needle target dome on said outer face of said septum.

49. An access port as recited in claim 48, wherein said needle target dome has an eccentricity in a range greater than 0.72.

50. An access port as recited in claim 48, wherein said needle target dome has an eccentricity in a range greater than 0.81.

51. An access port as recited in claim 48, wherein said needle target dome has an eccentricity in a range greater than 0.90.

52. An access port as recited in claim 48, wherein said needle target dome is smaller in extent than said outer face of said septum.

53. An access port as recited in claim 47, wherein said housing comprises:

(a) a base comprising a floor and a continuous encircling sidewall upstanding therefrom, the space interior of said sidewall of said base corresponding to said fluid reservoir of said housing; and (b) a cap comprising a top wall and a skirt depending therefrom, said cap being configured to receive in said skirt thereof the end of said sidewall of said base remote from said floor thereof, and said access aperture being formed through said top wall of said cap at a location that communicates with said fluid reservoir of said housing when said sidewall of said base is received in said skirt of said cap.

54. An access port as recited in claim 47, wherein said cross section of said septum taken in said plane thereof has an eccentricity in a range greater than about 0.72.

55. An access port as recited in claim 47, wherein said cross section of said septum taken in said plane thereof has an eccentricity in a range greater than about 0.81.

56. An access port as recited in claim 47, wherein said cross section of said septum taken in said plane thereof has an eccentricity in a range greater than about 0.90.

57. An access port as recited in claim 47, wherein said access aperture has an eccentricity in a range greater than about 0.72.

58. An access port as recited in claim 47, wherein said access aperture has an eccentricity in a range greater than about 0.81.

59. An access port as recited in claim 47, wherein said access aperture has an eccentricity in a range greater than about 0.90.

60. An access port as recited in claim 47, wherein:

(a) said septum has a longitudinal axis coincident with the maximum extent of said septum in said plane thereof, and a lateral axis coincident with the maximum extent of said septum in said plane thereof measured perpendicular to said longitudinal axis of said septum;

(b) the distance between a first pair of points on said periphery of said septum disposed on said longitudinal axis thereof is reduced in said installed configuration thereof relative to a natural configuration by a first compression distance;

(c) the distance between a second pair of points on said periphery of said septum disposed on said lateral axis is reduced in said installed configuration relative to said natural configuration by a second compression distance; and (d) the ratio of said first compression distance to the distance between said first pair of points in said natural configuration of said septum is equal to the ratio of said second compression distance to the distance between said second pair of points in said natural configuration of said septum.

61. An access port as recited in claim 47, wherein said cross section of said septum taken in said plane thereof is substantially elliptical.

62. An access port as recited in claim 47, wherein said cross section of said septum taken in said plane thereof is substantially oval.

63. An access port as recited in claim 47, wherein said septum has a longitudinal axis coincident with the maximum extent of said periphery of said septum in said cross section thereof taken in the plane thereof, said longitudinal axis of said septum intersects said periphery thereof at respective extreme end portions of said septum, and the periphery of each of said extreme end portions of said septum is substantially parabolic.

64. An implantable vascular access port comprising:

(a) a needle-impenetrable housing enclosing a fluid reservoir;

(b) an elastomeric, needle-penetrable, generally planar septum having an elongated periphery in a cross section of said septum taken in the plan thereof;

(c) access means formed in said housing between said fluid reservoir and the exterior of said housing for receiving said septum and for producing substantially uniform hydrostatic pressure in the portion of said septum accessible for needle penetration when said septum is received in said access means; and (d) an outlet stem projecting from said housing and enclosing a longitudinal fluid passageway extending from the end of said outlet stem remote from said housing through said housing to said fluid reservoir, said outlet stem having a longitudinal axis disposed parallel to said plane of said septum when said septum is received in said access means.

65. An access port as recited in claim 64, wherein said access means comprises:

(a) constriction means for displacing said periphery of said septum radially inwardly in said plane of said septum; and (b) clamp means for urging toward each other the opposite faces of said septum at said periphery thereof.

66. An access port as recited in claim 65, wherein said constriction means comprises an access aperture communicating between said fluid reservoir and the exterior of said housing, the rim of said access aperture being substantially geometrically proportional to and smaller than said periphery of said septum.

67. An access port as recited in claim 66, wherein said clamp means comprises:

(a) a septum retention lip projecting radially inwardly into said access aperture from the side of said rim thereof adjacent the exterior of said housing; and (b) a septum support shoulder projecting radially inwardly into said access aperture from the side of said rim opposite said septum retention lip, the distance between said septum retention lip and said septum support shoulder being less than the thickness of said septum between said opposite faces thereof at said periphery thereof.

68. An access port as recited in claim 67, further comprising a first septum gripping ridge projecting from and normal to said bearing surface of said septum retention lip.

69. An access port as recited in claim 68, further comprising a second septum gripping ridge projecting from said septum support shoulder opposite said septum support shoulder.

70. An access port as recited in claim 67, wherein said septum support shoulder comprises a continuous, encircling planar surface.

71. An access port as recited in claim 67, wherein the side of said septum retention lip opposite said septum support shoulder comprises a continuous, encircling planar surface.

72. An access port as recited in claim 64, wherein said access means comprises an access aperture communicating between said fluid reservoir and the exterior of said housing, the rim of said access aperture being substantially geometrically proportional to and smaller than said periphery of said septum, whereby said rim of said access aperture radially inwardly displaces said periphery of said septum when said septum is received in said access aperture.

73. An access port as recited in claim 64, wherein said access means comprises:

(a) an access aperture communicating between said fluid reservoir and the exterior of said housing and having an encircling continuous elongated rim;

(b) a septum retention lip projecting radially inwardly into said access aperture from the side of said rim thereof adjacent said exterior of said housing; and (c) a septum support shoulder projecting radially inwardly from said rim of said access aperture at the side thereof opposite said septum retention lip, said periphery of said septum being compressed between said septum retention lip and said septum support shoulder, when said septum is received in said access aperture.

74. An access port as recited in claim 64, wherein said periphery of said septum is substantially elliptical.

75. An implantable vascular access port comprising:

(a) a needle-impenetrable housing enclosing a fluid reservoir communicating with the exterior of said housing through an access aperture having a substantially elliptical rim and extreme ends defining therebetween the maximum extent of said access aperture;

(b) an outlet stem projecting from said housing at a location adjacent one of said extreme ends of said access aperture, said outlet stem enclosing a longitudinal fluid passageway extending from the end of said outlet stem remote from said housing through said housing to said fluid reservoir; and (c) an elastomeric, needle-penetrable, generally planar septum having a periphery in a cross section of said septum taken in the plane thereof that is substantially elliptical and that is larger than said rim of said access aperture, said septum being disposed in said access aperture with said periphery of said septum in sealing engagement with said rim of said access aperture, whereby in disposing said septum in said access aperture, said periphery of said septum is displaced radially inwardly by said rim of said access aperture in a direction parallel to said plane of said septum.

76. An access port as recited in claim 75, wherein said septum exhibits substantially uniform hydrostatic pressure in the portion of said septum accessible for needle penetration, when said septum is disposed in said access aperture.

77. An access port as recited in claim 76, wherein said substantially uniform hydrostatic pressure in the portion of said septum accessible for needle penetration is in a range from about 10 pounds per square inch to about 26 pounds per square inch.

78. An access port as recited in claim 75, wherein said periphery of said septum comprises an elongated polygon.

79. An access port as recited in claim 78, wherein said polygon has at least eight sides.

80. An access port as recited in claim 78, wherein said polygon has at most eight sides.

81. An access port as recited in claim 75, wherein said periphery of said septum is oval in shape.

82. An access port as recited in claim 75, wherein said septum has a longitudinal axis coincident with the maximum extent of said periphery of said septum in said cross section thereof taken in the plane thereof, said longitudinal axis of said septum intersects said periphery thereof at respective extreme end portions of said septum, and the periphery of each of said extreme end portions of said septum is substantially parabolic.

83. An access port as recited in claim 75, wherein said periphery of said septum is a true ellipse.

84. An access port as recited in claim 75, wherein said periphery of said septum is a continuous curve definable by a single mathematical equation.

85. An access port as recited in claim 75, wherein said septum is comprised of a material having a Shore "A" durometer in a range from about 45 to about 65.

86. An access port as recited in claim 75, wherein when said septum is disposed in said access aperture, said septum exhibits a substantially uniform needle retention force in a range from about 0.2 pounds to about 3.5 pounds.

87. An access port as recited in claim 75, wherein when said septum is disposed in said access aperture, said septum exhibits a substantially uniform needle retention force in a range from about 0.35 pounds to about 2.5 pounds.

88. An access port as recited in claim 75, wherein when said septum is disposed in said access aperture, said septum exhibits a substantially uniform needle retention force in a range from about 0.5 pounds to about 1.5 pounds.

* * * * *

UNITED STATES PATENT AND TRADEMARK OFFICE
CERTIFICATE OF CORRECTION

PATENT NO.      : 6,213,973 B1
DATED           : April 10, 2001
INVENTOR(S)     : Kenneth A. Eliasen, Kelly B. Powers and Kelly J. Christian It is certified that error appears in the above-identified patent and that said Letters Patent is hereby corrected as shown below:

<u>Title page,</u>
Item [75], change "Salt Lake" to -- Bountiful --
Item [56], change "(circa Aug. 1998)" to -- (circa Aug. 1995) --

<u>Column 2,</u>
Line 33, change "force.be" to -- force be --

<u>Column 3,</u>
Line 10, before "Septum" delete "S"

<u>Column 5,</u>
Line 65, change "substantial" to -- substantially --

<u>Column 7,</u>
Line 7, change "spetum" to -- septum --

<u>Column 8,</u>
Line 13, change "components.of" to -- components of --
Line 43, change "laterial; and" to -- lateral --

<u>Column 9,</u>
Line 33, delete "S"
Line 42, after "thereof" insert -- . --

<u>Column 10,</u>
Line 20, change "thereo.f" to -- thereof. --

<u>Column 11,</u>
Line 39, after "thereof" insert -- . --

<u>Column 12,</u>
Line 17, change "housing" to -- base --
Line 21, after "thereof" insert -- . --

<u>Column 17,</u>
Line 47, after "FIG. 9" delete ","
Line 48, after "1A" insert -- , --

UNITED STATES PATENT AND TRADEMARK OFFICE
CERTIFICATE OF CORRECTION

PATENT NO. : 6,213,973 B1
DATED : April 10, 2001
INVENTOR(S) : Kenneth A. Eliasen, Kelly B. Powers and Kelly J. Christian It is certified that error appears in the above-identified patent and that said Letters Patent is hereby corrected as shown below:

Column 18,
Line 24, delete "Equation" (first occurrence)
Line 24, change "No. 2;" to -- Equation No. 2, --

Column 20,
Line 38, change "cap 46" to -- cap 42 --
Line 52, change "shirt" to -- skirt --

Column 21,
Line 27, change "clamp," to -- , clamp --
Line 58, change "*near periphery 138*" to -- near periphery 138 --

Column 23,
Line 17, change ", therefor" to -- therefore --

Column 24,
Line 11, change "thereof" to -- of septum body 136 --

Column 27,
Line 31, after "There" insert -- , --

Column 28,
Line 39, change "." to -- , --

Column 30,
Line 25, change "bv" to -- by --
Line 26, after "shoulder" insert -- , --

Column 33,
Line 40, change "ofassuming" to -- of assuming --

Column 34,
Line 47, change "form" to -- from --

Column 35,
Line 61, after "configuration" insert -- thereof --

UNITED STATES PATENT AND TRADEMARK OFFICE
CERTIFICATE OF CORRECTION

PATENT NO.     : 6,213,973 B1
DATED          : April 10, 2001
INVENTOR(S)    : Kenneth A. Eliasen, Kelly B. Powers and Kelly J. Christian It is certified that error appears in the above-identified patent and that said Letters Patent is hereby corrected as shown below:

Replace Fig 9 with the following:

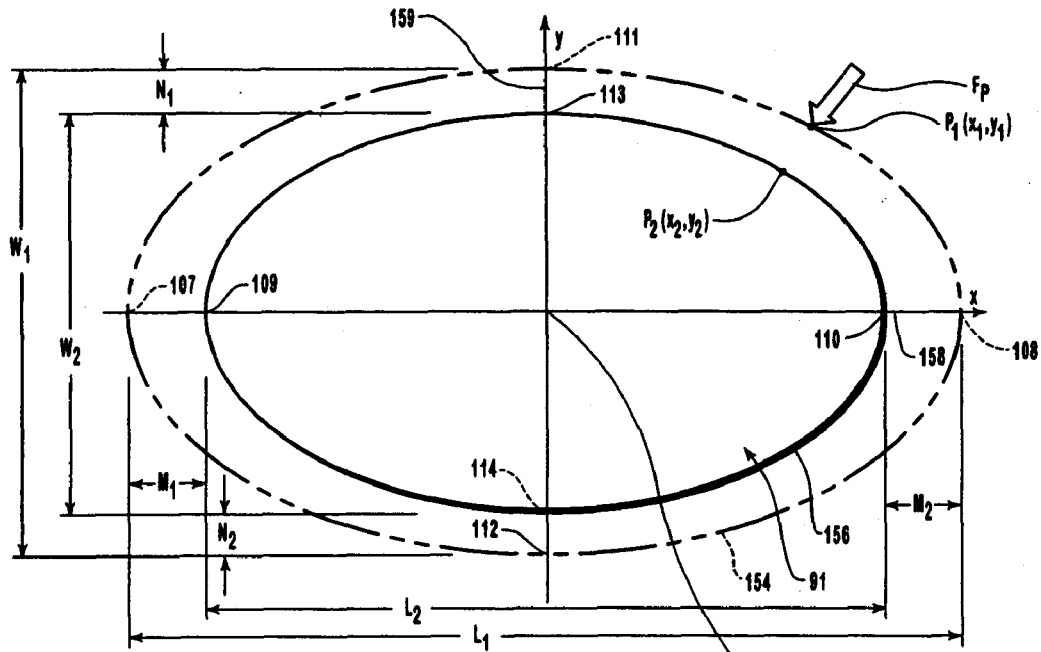

FIG. 9

UNITED STATES PATENT AND TRADEMARK OFFICE
CERTIFICATE OF CORRECTION

PATENT NO.   : 6,213,973 B1
DATED        : April 10, 2001
INVENTOR(S)  : Kenneth A. Eliasen, Kelly B. Powers and Kelly J. Christian It is certified that error appears in the above-identified patent and that said Letters Patent is hereby corrected as shown below:

Replace Fig 10 with the following:

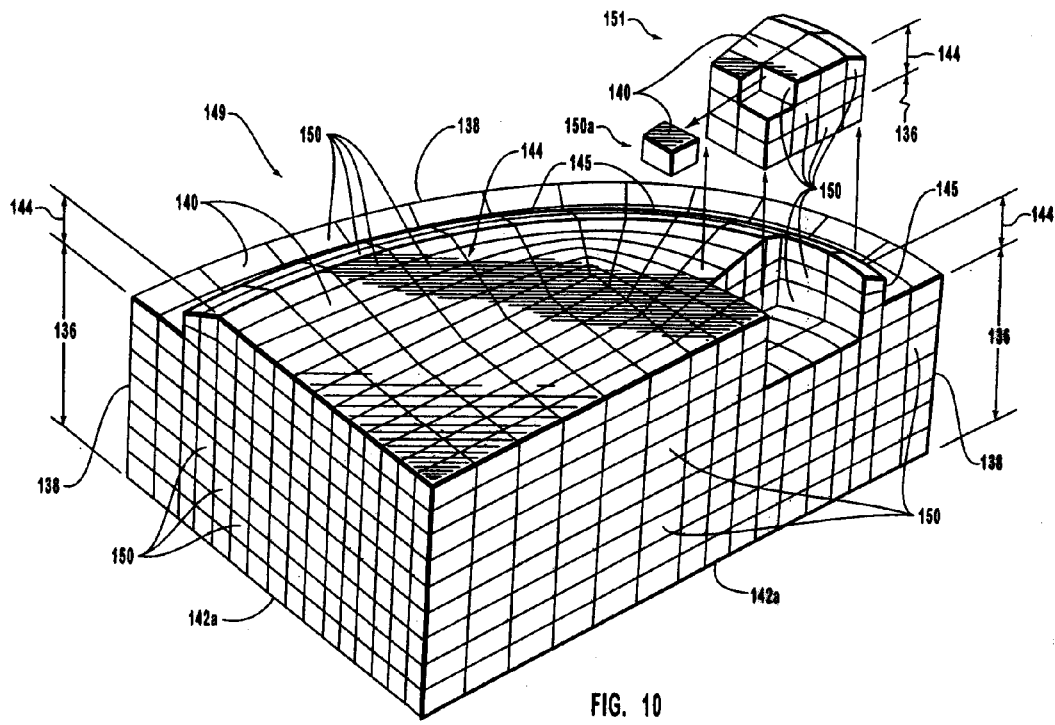

FIG. 10

Signed and Sealed this

Twelfth Day of November, 2002

*Attest:*

*Attesting Officer*

JAMES E. ROGAN
*Director of the United States Patent and Trademark Office*